(12) United States Patent
Buschmann

(10) Patent No.: US 10,577,698 B2
(45) Date of Patent: Mar. 3, 2020

(54) ELECTROCHEMICAL REACTOR AND PROCESS

(71) Applicant: Clean Chemistry, Inc., Boulder, CO (US)

(72) Inventor: Wayne E. Buschmann, Boulder, CO (US)

(73) Assignee: Clean Chemistry, Inc., Boulder, CO (US)

( * ) Notice: Subject to any disclaimer, the term of this patent is extended or adjusted under 35 U.S.C. 154(b) by 108 days.

(21) Appl. No.: 15/334,012

(22) Filed: Oct. 25, 2016

(65) Prior Publication Data

US 2017/0114468 A1 Apr. 27, 2017

Related U.S. Application Data

(63) Continuation of application No. 14/122,185, filed as application No. PCT/US2012/040325 on May 31, 2012, now Pat. No. 9,551,076.
(Continued)

(51) Int. Cl.
*C25B 1/30* (2006.01)
*C01B 7/01* (2006.01)
(Continued)

(52) U.S. Cl.
CPC ................ *C25B 1/30* (2013.01); *C01B 7/01* (2013.01); *C01B 11/06* (2013.01); *C01B 11/062* (2013.01); *C01B 15/00* (2013.01); *C01B 15/01* (2013.01); *C01B 15/027* (2013.01); *C01B 17/745* (2013.01); *C01D 1/04* (2013.01); *C07C 51/02* (2013.01); *C25B 1/00* (2013.01); *C25B 1/14* (2013.01); *C25B 1/22* (2013.01);
(Continued)

(58) Field of Classification Search
CPC .... C25B 1/00; C25B 1/14; C25B 1/22; C25B 1/24; C25B 1/26; C25B 1/265; C25B 1/30; C25B 1/34; C25B 3/02; C25B 9/00; C25B 9/08; C25B 15/02; C25B 15/08; C01B 7/01; C01B 11/06; C01B 11/062; C01B 15/00; C01B 15/01; C01B 15/027; C01B 17/745; C01D 1/04; C07C 51/02
See application file for complete search history.

(56) References Cited

U.S. PATENT DOCUMENTS 3,719,552 A 3/1973 Farley
3,925,234 A 12/1975 Hachmann et al.
(Continued)

FOREIGN PATENT DOCUMENTS

CN 1142555 2/1997
CN 102007230 4/2011
(Continued)

OTHER PUBLICATIONS

Non-Final Office Action for U.S. Appl. No. 14/122,185 dated Oct. 28, 2015.
(Continued)

*Primary Examiner* — Ciel P Thomas
(74) *Attorney, Agent, or Firm* — Snell & Wilmer LLP

(57) ABSTRACT

The electrochemical reactors disclosed herein provide novel oxidation and reduction chemistries and employ increased mass transport rates of materials to and from the surfaces of electrodes therein.

20 Claims, 7 Drawing Sheets

Related U.S. Application Data

(60) Provisional application No. 61/491,800, filed on May 31, 2011.

(51) Int. Cl.

| | | |
|---|---|---|
| *C01B 11/06* | (2006.01) | |
| *C01B 15/00* | (2006.01) | |
| *C01B 15/01* | (2006.01) | |
| *C01B 15/027* | (2006.01) | |
| *C01B 17/74* | (2006.01) | |
| *C01D 1/04* | (2006.01) | |
| *C07C 51/02* | (2006.01) | |
| *C25B 1/00* | (2006.01) | |
| *C25B 1/14* | (2006.01) | |
| *C25B 1/22* | (2006.01) | |
| *C25B 1/24* | (2006.01) | |
| *C25B 1/26* | (2006.01) | |
| *C25B 1/34* | (2006.01) | |
| *C25B 3/02* | (2006.01) | |
| *C25B 9/00* | (2006.01) | |
| *C25B 9/08* | (2006.01) | |
| *C25B 15/02* | (2006.01) | |
| *C25B 15/08* | (2006.01) | |

(52) U.S. Cl.
CPC ............. *C25B 1/24* (2013.01); *C25B 1/26* (2013.01); *C25B 1/265* (2013.01); *C25B 1/34* (2013.01); *C25B 3/02* (2013.01); *C25B 9/00* (2013.01); *C25B 9/08* (2013.01); *C25B 15/02* (2013.01); *C25B 15/08* (2013.01)

(56) References Cited

U.S. PATENT DOCUMENTS

| | | | |
|---|---|---|---|
| 4,055,505 A | 10/1977 | Gray | |
| 4,076,621 A | 2/1978 | Hardison | |
| 4,348,256 A | 9/1982 | Bergstrom, Jr. et al. | |
| 4,393,037 A | 7/1983 | Delaney et al. | |
| 4,576,609 A | 3/1986 | Hageman | |
| 4,673,473 A | 6/1987 | Ang et al. | |
| 4,722,773 A * | 2/1988 | Plowman | C25B 1/46 204/252 |
| 4,952,276 A | 8/1990 | Gidlund | |
| 4,966,706 A | 10/1990 | Gregor | |
| 5,053,142 A | 10/1991 | Sorensen et al. | |
| 5,246,543 A | 9/1993 | Meier et al. | |
| 5,387,317 A | 2/1995 | Parthasarathy et al. | |
| 5,424,032 A | 6/1995 | Christensen et al. | |
| 5,431,781 A | 7/1995 | Walsh | |
| 5,472,619 A | 12/1995 | Holzhauer et al. | |
| 5,494,588 A | 2/1996 | LaZonby | |
| 5,565,073 A * | 10/1996 | Fraser | C25B 1/30 204/256 |
| 5,683,724 A | 11/1997 | Hei et al. | |
| 5,770,035 A * | 6/1998 | Faita | C25B 1/26 205/640 |
| 5,785,812 A | 7/1998 | Linsten et al. | |
| 5,817,240 A | 10/1998 | Miller et al. | |
| 6,007,678 A | 12/1999 | Linsten et al. | |
| 6,015,536 A | 1/2000 | Lokkesmoe et al. | |
| 6,126,782 A | 10/2000 | Liden et al. | |
| 6,183,623 B1 | 2/2001 | Cisar et al. | |
| 6,258,207 B1 | 7/2001 | Pan | |
| 6,387,238 B1 | 5/2002 | Merk et al. | |
| 6,569,286 B1 | 5/2003 | Withenshaw et al. | |
| 6,712,949 B2 * | 3/2004 | Gopal | C25B 1/30 204/263 |
| 8,318,972 B2 | 11/2012 | Buschmann et al. | |
| 9,517,955 B2 | 12/2016 | Buschmann | |
| 9,517,956 B2 | 12/2016 | Buschmann | |
| 9,551,076 B2 | 1/2017 | Buschmann | |
| 10,259,729 B2 | 4/2019 | Buschmann | |
| 2001/0050234 A1 | 12/2001 | Shiepe | |
| 2002/0153262 A1 * | 10/2002 | Uno | C25B 1/30 205/466 |
| 2003/0019757 A1 * | 1/2003 | Vetrovec | C25B 1/30 205/466 |
| 2003/0019758 A1 | 1/2003 | Gopal | |
| 2003/0024054 A1 | 2/2003 | Burns | |
| 2004/0112555 A1 | 6/2004 | Tolan et al. | |
| 2004/0134857 A1 | 7/2004 | Huling et al. | |
| 2004/0200588 A1 | 10/2004 | Walker | |
| 2005/0183949 A1 | 8/2005 | Daly | |
| 2006/0207734 A1 | 9/2006 | Day | |
| 2007/0212594 A1 | 9/2007 | Takasu et al. | |
| 2007/0243449 A1 | 10/2007 | Sotomura et al. | |
| 2009/0012346 A1 | 1/2009 | Al Nashef et al. | |
| 2009/0090478 A1 | 4/2009 | Hollomon et al. | |
| 2009/0152123 A1 | 6/2009 | Butler et al. | |
| 2009/0285738 A1 | 11/2009 | Winter et al. | |
| 2009/0314652 A1 | 12/2009 | Buschmann et al. | |
| 2010/0078331 A1 * | 4/2010 | Scherson | C25B 1/24 205/335 |
| 2010/0160449 A1 | 6/2010 | Rovison, Jr. et al. | |
| 2010/0176066 A1 | 7/2010 | Budde et al. | |
| 2010/0179368 A1 | 7/2010 | Conrad | |
| 2011/0017066 A1 | 1/2011 | Takeuchi et al. | |
| 2011/0024361 A1 | 2/2011 | Schwartzel et al. | |
| 2011/0123642 A1 | 5/2011 | Wilmotte | |
| 2011/0232853 A1 | 9/2011 | Yin | |
| 2012/0067532 A1 | 3/2012 | Lee | |
| 2012/0091069 A1 | 4/2012 | Fischmann | |
| 2012/0108878 A1 | 5/2012 | Conrad | |
| 2012/0145643 A1 | 6/2012 | Pandya | |
| 2012/0240647 A1 | 9/2012 | Montemurro | |
| 2012/0267315 A1 | 10/2012 | Soane et al. | |
| 2012/0322873 A1 | 12/2012 | Atkins et al. | |
| 2013/0259743 A1 | 10/2013 | Keasler et al. | |
| 2013/0264293 A1 | 10/2013 | Keasler et al. | |
| 2014/0069821 A1 | 3/2014 | Marcin et al. | |
| 2014/0072653 A1 | 3/2014 | Buschmann | |
| 2014/0131217 A1 | 5/2014 | Buschmann | |
| 2014/0131259 A1 | 5/2014 | Goldblatt | |
| 2014/0205777 A1 | 7/2014 | Hawkins et al. | |
| 2014/0238626 A1 | 8/2014 | Tsuji et al. | |
| 2014/0374104 A1 | 12/2014 | Seth | |
| 2016/0068417 A1 | 3/2016 | Buschmann | |
| 2016/0297697 A1 | 10/2016 | Buschmann | |
| 2016/0318778 A1 | 11/2016 | Buschmann | |
| 2017/0051417 A1 | 2/2017 | Buschmann | |
| 2017/0107128 A1 | 4/2017 | Buschmann | |
| 2017/0158537 A1 | 6/2017 | Buschmann | |
| 2017/0159237 A1 | 6/2017 | Buschmann | |

FOREIGN PATENT DOCUMENTS

| | | |
|---|---|---|
| EP | 0480469 A3 | 4/1992 |
| WO | 9402423 A1 | 2/1994 |
| WO | 9739179 A1 | 10/1997 |
| WO | 1999032710 | 7/1999 |
| WO | 2000069778 | 11/2000 |
| WO | 2008056025 A2 | 5/2008 |
| WO | 2010059459 | 5/2010 |
| WO | 2012166997 | 12/2012 |
| WO | 2013060700 A1 | 5/2013 |
| WO | 2013064484 | 5/2013 |
| WO | 2014039929 | 3/2014 |
| WO | 2014100828 | 6/2014 |
| WO | 2016037149 | 3/2016 |
| WO | 2016154531 | 9/2016 |
| WO | 2017100284 | 6/2017 |
| WO | 2017100299 | 6/2017 |

OTHER PUBLICATIONS

Final Office Action for U.S. Appl. No. 14/122,185 dated Jul. 28, 2016.
CC03—First Office Action for Chinese Application No. 2013800580496 dated Feb. 4, 2016.

(56) References Cited

OTHER PUBLICATIONS

CC05—Supplementary Partial European Search Report for European Application No. EP 13 83 4576 dated May 10, 2016.
CC04—International Search Report for PCT/US2015/048722 dated Feb. 8, 2016.
CC15—Suslow, T. "Oxidation-Reduction Potential (ORP) for Water Disinfection Monitoring, Control, and Documentation" Univ. California Publication 8149 http://anrcatalog.ucdavis.edu, Copyright 2004.
Co-Pending U.S. Appl. No. 15/601,350 entitled, "Methods of Pulp Fiber Treatment" to Buschmann filed May 22, 2017.
Co-Pending U.S. Appl. No. 15/658,709 entitled, "Methods of Optical Brightening Agent Removal" to Buschmann filed Jul. 25, 2017.
CC16—L.D. Shackford, "A Comparison of Pulping and Bleaching of Kraft Softwood and Eucalyptus Pulps;" 36th International Pulp and Paper Congress and Exhibition; Oct. 13-16, 2003, Sao Paulo, Brazil.
Notice of Allowance for U.S. Appl. No. 14/122,185 dated Oct. 13, 2016.
Notice of Allowance for U.S. Appl. No. 14/020,828 dated Aug. 11, 2016.
CC06—International Preliminary Report on Patentability for PCT/US2013/058650 dated Jan. 29, 2014.
CC07—Australian Examination Report No. 1 for 2013312249 dated Mar. 17, 2017.
CC08—Second Office Action for Chinese Application No. 2013800580496 dated Sep. 18, 2016.
CC09—Extended European Search Report for European Application No. EP 13 83 4576 dated Oct. 4, 2016.
Notice of Allowance for U.S. Appl. No. 15/206,901 dated Aug. 17, 2016.
Restriction for U.S. Appl. No. 14/846,123 dated Sep. 7, 2017.
CC10—International Preliminary Report on Patentability for PCT/US2015/048722 dated Feb. 8, 2016.
CC11—International Preliminary Report on Patentability for PCT/US2016/024207 dated Sep. 26, 2017.
CC12—International Search Report for PCT/US2016/065326 dated Feb. 24, 2017.
Non-Final Office Action for U.S. Appl. No. 15/371,872 dated Oct. 12, 2017.
CC13—International Search Report for PCT/US2016/065345 dated Feb. 17, 2017.
CC14—International Search Report for PCT/US2017/033824 dated Aug. 29, 2017.
CC01—International Search Report for PCT/US2012/040325 dated Feb. 1, 2013.
CC02—International Search Report for PCT/US2013/058650 dated Jan. 29, 2014.
Non-Final Office Action for U.S. Appl. No. 14/020,828 dated Jan. 20, 2016.
Notice of Allowance for U.S. Appl. No. 14/020,828 dated Mar. 30, 2016.
Suihko et al.; "A study of the microflora of some recyled fibre pulps, boards and kitchen rolls"; The Journal of Applied Microbiology; 1997; vol. 83; pp. 199-207.
Suslow; "Oxidation-Reduction Potential (ORP) for Water Disinfection Monitoring, Control, and Documentation"; Univ. California; 2004; Publication 8149; 5 pgs.; http://anrcatalog.ucdavis.edu.
Pedros et al.; "Chlorophyll fluorescence emission spectrum inside a leaf"; The Royal Society of Chemistry and Owner Societies; 2008; No. 7; pp. 498-502.
Coyle et al.; "Peracetic Acid as an Alternative Disinfection Technology for Wet Weather Flows"; Water Environment Research; Aug. 2014; pp. 687-697.
Smook; "Chapter 14: Secondary Fiber"; Handbook for Pulp & Papers Technologists; Angus Wilde Publications; 2001; pp. 209-219.
Gullichsen et al., eds.; Chemical Pulping; Papermaking Science and Technology; Book 6A; 1999; Fapet Oy; pp. A40-A41 and A616-A665.
Hill et al.; "Part 1: Peracetic Acid—An effective alternative for Chlorine compound Free Delignification of Kraft Pulp"; 1992; Pulping Conference; pp. 1219-1230.
Verween et al.; "Comparative toxicity of chlorine and peracetic acid in the biofouling control of Mytilopsis leucophaeata and Dreissena polymorpha embryos (Mollusca, Bivalvia)"; International Biodeterioration & Biodegradation; vol. 63, No. 4; 2009; pp. 523-528.

* cited by examiner

ELECTROCHEMICAL REACTOR AND PROCESS

RELATED APPLICATIONS

This application is a continuation of U.S. patent application Ser. No. 14/122,185 entitled "ELECTROCHEMICAL REACTOR AND PROCESS" filed on Nov. 25, 2013, which is a National Stage Entry of PCT/US2012/040325 entitled "ELECTROCHEMICAL REACTOR AND PROCESS" filed on May 31, 2012, which claims the benefit of priority of U.S. Provisional Application Ser. No. 61/491,800 filed May 31, 2011, all of which are incorporated herein by reference in their entirety.

BACKGROUND

The economic scale up of electrochemical reactors and processes has been challenging due to the low economy of scale factor inherent to such devices. This challenge can be encountered by electrochemical processes including electrowinning, electrorefining, electroplating, electrocoagulation, hypochlorite and disinfectant generation, hydrogen generation, and fuel cell and battery operation. A variety of factors can play a role in the inability to economically build and operate scaled up electrochemical reactors and processes.

Generally speaking, productivity in electrochemical reactors and processes is directly proportional to the electrode area and current density at a given efficiency. Accordingly, scale up tends to require larger electrodes, an increased number of electrodes, and/or increased power demands, all of which raise the cost of operating the electrochemical reactor and process.

Productivity can also be a challenge when the electrochemical process is limited in rate due to the kinetics of the desired transformative processes and mass transport. Additional challenges are encountered when secondary processes are competing with the desired transformation. Particularly challenging are electrochemical processes involving several steps along the reaction pathway resulting in the slow transformation of reactants to products and lower productivity. Such steps can include dissolution, diffusion, electrode or catalyst surface adsorption/desorption, electron transfer, ion transfer, molecular rearrangement, breaking or making of chemical bonds, and chemical reactions of intermediates. Further complicating matters is that the desired process may occur at a similar electrode potential (voltage) as other undesired processes, such as side reactions that consume electricity, may consume the desired product or produce a poor product. The aforementioned issue of poor process selectivity can also lead to reduced productivity.

A variety of methods are employed to compensate for slow kinetics, limited mass transport and reduced selectivity of certain electrochemical processes. Some of the most common methods include the use of high surface area electrodes, process-selective electrocatalysts, pH adjustment, temperature control, chemical additives, elevated reactant concentration, mixing and turbulence, separation of electrode processes, potential control, and minimizing shunt losses or shorting (both electrical and chemical). The above list is only exemplary as there are many useful methods demonstrated in the literature. The aforementioned methods are effective for optimizing single phase electrochemical reaction processes in general, but are not as effective or practical for optimizing multiphase electrochemical processes.

Electrochemical processes that involve the interaction of multiple phases at an electrode surface, such as gas and liquid, add another level of challenge when designing highly productive electrochemical devices. Achieving uniform distribution of gas and liquid components over large-scale electrodes is challenging from a practical design and operations perspective. Often, the multiphase electrochemical process involves the transformation of gas-phase materials (such as the reduction of oxygen or carbon dioxide), which must be present at the electrode surface simultaneously with the liquid (electrolyte) phase for a transformation to occur. Examples of reactors designed to afford high surface area access to gaseous and liquid phases include those employing gas diffusion electrodes, packed beds of conductive particles, dimensionally stable porous conductive media, rotating electrodes, vortex-flow or high sheer flow electrodes. Many of the above multi-phase reactor approaches are feasible in the laboratory, but few are practical for economic scale up, production, and operation.

Particularly desirable applications of electrochemical reactors are on-site, mobile, and distributed systems for generating cleansers and disinfectants, decontamination and remediation, water treatment and recycle, waste treatment, and chemical production. The design of a cost-effective multi-phase electrochemical reactor is critical to making several potential applications commercially viable. Although electrochemical systems are not cost competitive to many bulk commodity chemical manufacturing processes at the largest scales, they do offer cost advantages for medium to small distributed applications, remote operations, and rapid deployment systems while helping to reduce transportation costs and provide safety advantages for end-users, facilities, and populations around transportation corridors.

Electrochemical reactors should ideally be compact, convenient and safe to operate in a variety of settings without extensive supporting utilities or infrastructure. Examples of application settings include, but are not limited to, laundry machines, clean-in-place equipment, desalination membrane cleaning, food service cleansing applications, medical facilities, dairy and farming operations, trailer-mounted environmental remediation and decontamination systems, remote site chemical generation and waste treatment (mining, offshore oil rigs, marine vessels), and on-site management of highly toxic and radiation-contaminated waste.

The use of multi-phase electrochemical reactors is desirable for enabling cathodic processes, with known examples including hydrogen peroxide production, cleanser generation, co-generation of products, nitrate destruction, electrolytic water treatment, dechlorination, deozonation, and carbon dioxide reduction to fuels or chemicals. Potentially valuable cathodic processes involve the reduction of reactants such as oxygen or oxides (e.g., nitrate, nitrite, nitrous oxides, carbon dioxide) to various products. Reduction of such materials is a kinetically slow process resulting in low specific current densities (less than approximately 1000 $A/m^2$ specific electrode area) or poor current efficiency for the desired process. Likewise, concentrations of such materials are often low or diffusion limiting, thus further inhibiting reaction rates, specific current density, efficiency and overall productivity. The above issues result in capital costs that make such electrochemical processes cost prohibitive.

The use of such reactors can also be desirable for enabling anodic processes to be conducted without the generation of hydrogen gas as a process byproduct by means of an oxygen depolarized cathode. This capability is a useful for operations in confined spaces where the risk of flammable gas buildup is undesired, such as in occupied buildings, marine vessels, and underground mining operations. Examples of anodic processes include chlorine, hypochlorous acid and hypochlorite generation, ammonia oxidation, desulfurization and deodorization of gases, organic contaminant destruction, and electrocoagulation. The use of such reactors can also enable co-generation of several of the above products or combining processes depending on the combination of inputs.

SUMMARY

Described herein are various embodiments of a novel apparatus for use as an electrochemical reactor and novel electrochemical processes. The reactor and associated process are designed for promoting efficient and productive electrochemical transformation of material fed into the reactor in the presence of at least two phases. The electrochemical reactor and process described herein are particularly useful for carrying out cathodic electrochemical processes involving the use of multiple phases. Potentially valuable cathodic processes which can be carried out using the electrochemical reactor described herein involve the reduction of reactants such as oxygen or oxides (e.g., nitrate, nitrite, nitrous oxides, carbon dioxide) to various products. The electrochemical reactor and process described herein are designed to increase productivity for multi-phase electrochemical processes by compensating for lower specific current density with increased active electrode surface area per unit superficial area, increase mass transfer rates, increased process selectivity or efficiency, and by being designed and packaged in a durable, cost-effective format for affordability and cost-competitiveness in small to medium scale distributed and mobile applications.

In some embodiments, the electrochemical reactor includes a cathode and an anode. The cathode and anode are separated by an ion-permeable separator. The cathode is located in a cathode chamber defined by the ion-permeable separator on one side and a gas distributor on the opposite side. The anode is located in an anode chamber defined by the ion permeable separator on one side and a containment boundary on the other side. A gas chamber is also defined between the containment boundary and the gas distributor. In some embodiments, the electrochemical reactor has an annular or tubular configuration, with the containment boundary serving as the outer most ring and the gas distributor serving as the inner most ring. The anode ring is closest to the containment boundary and the cathode ring is closest to the gas distributor. A separator ring is position between the cathode and the anode.

In some embodiments, the electrochemical process includes providing a cathode in a cathode chamber and an anode in an anode chamber, wherein the cathode chamber and anode chamber are separated by an ion-permeable separator and wherein the boundary of the cathode chamber opposite the ion-permeable separator is a gas distributor; flooding the cathode chamber with a catholyte and flooding the anode chamber with an anolyte; dispersing a gas phase into the cathode chamber through the gas distributor; applying a voltage to the cathode and anode; and allowing a multiphase electrochemical reaction to progress.

In one aspect, disclosed herein is an electrochemical reactor for producing chemical species, the electrochemical reactor comprising a first half-cell comprising an anode electrode and an anolyte, a second half-cell comprising a cathode electrode and a catholyte, a gas distributor introduces gas adjacent to at least one of the anode electrode and/or the cathode electrode and an ion permeable separator separating the first half-cell and the second half-cell. In one embodiment, the electrochemical reactor is disclosed wherein the chemical species produced is determined according to the composition of the anolyte, the composition of the catholyte, the composition of the gas distributed adjacent to at least one of the anode electrode and/or the cathode electrode, and the ion permeability of the ion permeable separator. In another embodiment, the electrochemical reactor is disclosed wherein the chemical species produced is determined according to the pH of the anolyte, the pH of the catholyte, the voltage applied to the anode electrode, the electric current applied to the anode electrode, the voltage applied to the cathode electrode, and the electric current applied to the cathode electrode. In an embodiment, the electrochemical reactor is disclosed wherein the gas feed volume flow rate to the cathode electrode and/or anode electrode is from about 100 to about 1400 times greater than the liquid anolyte or liquid catholyte flow rate. In an embodiment, the electrochemical reactor is disclosed wherein the cathode electrode exhibits electroactivity over greater than 50% of its specific surface area, and the cathode electrode has a specific surface area greater than about 1 $m^2$ per 1 $m^2$ superficial area, preferably a specific surface area greater than about 5 $m^2$ per 1 $m^2$ superficial area, more preferably a specific surface area greater than about 10 $m^2$ per 1 $m^2$ superficial area, and even more preferably a specific surface area greater than about 100 $m^2$ per 1 $m^2$ superficial area. In an embodiment, the electrochemical reactor is disclosed wherein the composition of the gas is from about 20% oxygen to about 93% oxygen. In an embodiment, the electrochemical reactor is disclosed wherein the chemical species produced are selected from the group consisting essentially of hydrogen peroxide, superoxide, alkali, acids, citric acid, sodium hypochlorite, hypochlorites, sulfate acids, chlorine, and chlor-alkali.

In an embodiment, a method for using a flow pathway in the electrochemical reactor is disclosed to produce at least one product chemical species, the flow pathway comprises introducing the liquid anolyte into the first half-cell wherein at least one chemical species of the liquid anolyte is oxidized at the anode electrode, and introducing the liquid catholyte into the second half-cell wherein the gas distributor introduces the gas into the liquid catholyte and creates a multi-phase catholyte solution, and wherein the gas distributor introduces the gas into the cathode electrode, and wherein at least one chemical species of the multiphase catholyte solution is reduced at the cathode electrode, and wherein the reduced multiphase catholyte solution and/or the oxidized liquid anolyte contains the at least one product chemical species, and wherein the reduced multiphase catholyte solution flows out of the second half-cell, and wherein the oxidized liquid anolyte flows out of the first half-cell. In another embodiment a method is disclosed wherein the at least one product chemical species is selected from the group consisting essentially of: hydrogen peroxide, superoxide, alkali, acids, citric acid, sodium hypochlorite, hypochlorites, sulfate acids, chlorine, and chlor-alkali.

In another aspect, an electrochemical reactor is disclosed for reducing and/or oxidizing chemical species, the electrochemical reactor comprising a first half-cell comprising an anode electrode and an anolyte, a second half-cell comprising a cathode electrode and a catholyte, a gas distributor introduces gas adjacent to at least one of the anode electrode and/or the cathode electrode and an ion permeable separator separating the first half-cell and the second half-cell.

In yet another embodiment, a method for using a flow pathway in the electrochemical reactor to reduce and/or oxidize at least one chemical species is disclosed and the flow pathway comprises introducing the liquid anolyte into the first half-cell wherein at least one chemical species of the liquid anolyte is oxidized at the anode electrode, and introducing the liquid catholyte into the second half-cell wherein the gas distributor introduces the gas into the liquid catholyte and creates a multiphase catholyte solution, and wherein the gas distributor introduces the gas into the cathode electrode, and wherein at least one chemical species of the multiphase catholyte solution is reduced at the cathode electrode, and wherein the reduced multiphase catholyte solution and/or the oxidized liquid anolyte contains the at least one chemical species that has been reduced and/or oxidized, and wherein the reduced multiphase catholyte solution flows out of the second half-cell, and wherein the oxidized liquid anolyte flows out of the first half-cell. In an embodiment, the at least one chemical species that has been reduced and/or oxidized are selected from the group consisting essentially of molecular oxygen, hydroxyl radicals, hydroxide ions, hydrogen ions, hydrogen peroxide, superoxide, oxygen, water, alkali, acids, citric acid, sodium hypochlorite, hypochlorites, sulfate acids, hypochlorous acid, chlorine, and chlor-alkali.

In an aspect, an electrochemical reactor is disclosed and it comprises a containment boundary, a gas chamber, a gas distributor, a cathode chamber, a three dimensional cathode, a separator, an anode chamber, a three dimensional anode, and the containment boundary contains the gas chamber, the gas distributor, the cathode chamber, the three dimensional cathode, the separator, the anode chamber, the three dimensional anode, and the gas chamber is defined on a first side by the containment boundary and on a second side by a first side of the gas distributor, and a second side of the gas distributor is in contact with and defines a first side of the cathode chamber, and the cathode chamber is further defined on a second side by a first side of the separator, and the cathode chamber contains the three dimensional cathode, and the anode chamber is in contact with and defined on a first side by a second side of the separator, and the anode chamber is further defined on a second side by the containment boundary, and the anode chamber contains a three dimensional anode. In an embodiment, the electrochemical reactor is disclosed wherein the superficial area of the second side of the gas distributor is equal to or greater than the superficial area of a side of the three dimensional cathode that faces the second side of the gas distributor, and the superficial area of the second side of the gas distributor is separate from the three dimensional cathode In another embodiment, a method for using a flow pathway in the electrochemical reactor is disclosed to produce at least one chemical species, the flow pathway comprises introducing an anolyte flow into the anode chamber wherein at least one chemical species of the anolyte flow is oxidized at the three dimensional anode, and introducing a catholyte flow into the cathode chamber wherein the gas distributor introduces a gas into the catholyte flow and creates a multiphase catholyte solution, and the gas distributor introduces the gas into the three dimensional cathode, and at least one chemical species of the multiphase catholyte solution is reduced at the three dimensional cathode, and the reduced multiphase catholyte solution flows out of the cathode chamber, and the oxidized anolyte flow flows out of the anode chamber, and the reduced multiphase catholyte solution and/or the oxidized anode flow contains the at least one chemical species produced.

In an aspect, a tubular electrochemical reactor is disclosed that comprises a tubular gas chamber, a tubular gas dispersion tube, a cathode flow channel, a tubular cathode, a tubular separator, a tubular anode, a tubular anolyte chamber, a tubular anolyte chamber housing, and the tubular gas chamber resides within and is defined by the interior surface of the tubular gas dispersion tube, and the exterior surface of the tubular gas dispersion tube forms the interior side of the cathode flow channel, and the interior surface of the tubular separator forms the exterior side of the cathode flow channel, and the tubular cathode resides within the cathode flow channel, and the exterior surface of the tubular separator forms the interior side of the tubular anolyte chamber, and the exterior side of the tubular anolyte chamber is formed by the interior surface of the tubular anolyte chamber housing, and the tubular anode resides within the tubular anolyte chamber. In an embodiment, the tubular electrochemical reactor disclosed further comprises a first toroidal seat plate, a second toroidal seat plate, a first end plate, a second end plate, a first toroidal cathode current distributor and compression ferrule, a second toroidal cathode current distributor and compression ferrule, and a second side of the first toroidal seat plate forms a first end of the tubular anolyte chamber by bridging a first end of the interior surface of the tubular anolyte chamber housing at an exterior portion of the first toroidal seat plate and a first end of the exterior surface of the tubular separator at an interior portion of the first toroidal seat plate, and a first side of the second toroidal seat plate forms a second end of the tubular anolyte chamber by bridging a second end of the interior surface of the tubular anolyte chamber housing at an exterior portion of the second toroidal seat plate and a second end of the exterior surface of the tubular separator at an interior portion of the second toroidal seat plate, and a second side of the first toroidal cathode current distributor and compression ferrule contacts a first end of the tubular cathode, and the second side of the first toroidal cathode current distributor and compression ferrule bridges a first end of the tubular separator and a interior surface of the first toroidal seat plate, and a first side of the second toroidal cathode current distributor and compression ferrule contacts a second end of the tubular cathode, and the first side of the second toroidal cathode current distributor and compression ferrule bridges a second end of the tubular separator and a interior surface of the second toroidal seat plate, and a second side of the first end plate forms a first end of the tubular gas chamber, and the second side of the first end plate forms a first end of the tubular gas dispersion tube, and the second side of the first end plate compresses the first toroidal cathode current distributor and compression ferrule between the second side of the first end plate and the first side of the first toroidal seat plate, and a first side of the second end plate forms a second end of the tubular gas chamber, and the first side of the second end plate forms a second end of the tubular gas dispersion tube, and the first side of the second end plate compresses the second toroidal cathode current distributor and compression ferrule between the first side of the second end plate and a second side of the second toroidal seat plate. In another embodiment, the tubular electrochemical reactor disclosed further comprises at least one cathode electrical feed through post in the first and the second end plate, at least one catholyte inlet/outlet port in the first and the second end plate, at least one gas inlet/outlet port in the first and the second end plate, at least one anolyte inlet/outlet port in the tubular anolyte chamber housing, at least one anode electrical feed through post that passes through the tubular anolyte chamber housing and makes contact with the tubular anode at at least one anode current collector tab. In another embodiment, the tubular electrochemical reactor is disclosed wherein a second end of the at least one cathode electrical feed through post contacts a first toroidal cathode current distributor and compression ferrule, and a first end of the at least one cathode electrical feed through post protrudes from a first side of the first end plate, and a first end of the at least one cathode electrical feed through post contacts a second toroidal cathode current distributor and compression ferrule, and a second end of the at least one cathode electrical feed through post protrudes from a second side of the second end plate. In another embodiment, the tubular electrochemical reactor is disclosed wherein at least one catholyte inlet/outlet port in the first and the second end plate forms a channel with the cathode flow channel, and at least one gas inlet/outlet port in the first and the second end plate forms a channel with the tubular gas chamber, and at least one anolyte inlet/outlet port in the tubular anolyte chamber housing forms a channel with the tubular anolyte chamber.

In another embodiment, a method for using a flow pathway in the tubular electrochemical reactor is disclosed that produces at least one chemical species, the flow pathway comprises introducing an anolyte flow into the tubular anolyte chamber wherein at least one chemical species of the anolyte flow is oxidized at the tubular anode, and introducing a catholyte flow into the cathode chamber wherein the tubular gas distributor introduces a gas into the catholyte flow and creates a multiphase catholyte solution, and the tubular gas distributor introduces the gas into the tubular cathode, and at least one chemical species of the multiphase catholyte solution is reduced at the tubular cathode, and the reduced multiphase catholyte solution and/or the oxidized anode flow contains the at least one chemical species produced, and the reduced multiphase catholyte solution flows out of the cathode chamber, and the oxidized anolyte flow flows out of the tubular anolyte chamber. In another embodiment, the tubular electrochemical reactor is disclosed wherein the tubular separator is selectively permeable to cations. In yet another embodiment, the tubular electrochemical reactor is disclosed wherein the tubular separator is selectively permeable to anions. In another embodiment, the tubular electrochemical reactor is disclosed wherein the tubular cathode has a thickness that is between about 0.1 and 10 millimeters, and preferably between about 0.5 and 5 millimeters and more preferably between about 1 and 3 millimeters. In an embodiment, the tubular electrochemical reactor is disclosed wherein the tubular cathode exhibits electroactivity over greater than 50% of its specific surface area, and the tubular cathode has a specific surface area greater than about 1 $m^2$ per 1 $m^2$ superficial area, preferably a specific surface area greater than about 5 $m^2$ per 1 $m^2$ superficial area, more preferably a specific surface area greater than about 10 $m^2$ per 1 $m^2$ superficial area, and even more preferably a specific surface area greater than about 100 $m^2$ per 1 $m^2$ superficial area.

In an embodiment, a method of making hydrogen peroxide is disclosed that makes hydrogen peroxide by providing the electrochemical reactor with a catholyte feed, an anolyte feed, a gas feed, a voltage to the tubular cathode, and a voltage to the tubular anode. In another embodiment, a method is disclosed for making superoxide by providing the electrochemical reactor with a catholyte feed, an anolyte feed, a gas feed, a voltage to the tubular cathode, and a voltage to the tubular anode. In yet another embodiment, a method of making a mixture of hydrogen peroxide and superoxide in the cathode flow channel of the electrochemical reactor is disclosed the mixture of hydrogen peroxide and superoxide is made by providing a catholyte feed, an anolyte feed, a gas feed, a voltage to the tubular cathode, and a voltage to the tubular anode of the electrochemical reactor. In another embodiment, disclosed is a method of making alkaline hydrogen peroxide and citric acid by providing the electrochemical reactor with a catholyte feed, an anolyte feed, a gas feed, a voltage to the tubular cathode, and a voltage to the tubular anode. In another embodiment, disclosed is a method of making alkaline hydrogen peroxide and sulfate acids by providing the electrochemical reactor with a catholyte feed, an anolyte feed, a gas feed, a voltage to the tubular cathode, and a voltage to the tubular anode. In yet another embodiment, disclosed is a method of making alkaline hydrogen peroxide and sodium hypochlorite by providing the electrochemical reactor with a catholyte feed, an anolyte feed, a gas feed, a voltage to the tubular cathode, and a voltage to the tubular anode.

The foregoing and other features and advantages of the embodiments disclosed herein will become more apparent from the following description.

DETAILED DESCRIPTION

Electrochemical Reactor

Disclosed herein are embodiments of an electrochemical reactor and processes for causing an electrochemical (electrolytic or electrocatalytic) transformation of material fed into the electrochemical reactor. In an embodiment, the electrochemical processes disclosed herein involve at least two phases of matter, e.g. liquid and gas, and optionally a combination of one or more elemental, molecular, ionic or chemical species contained within such phases of matter.

Figure 1:
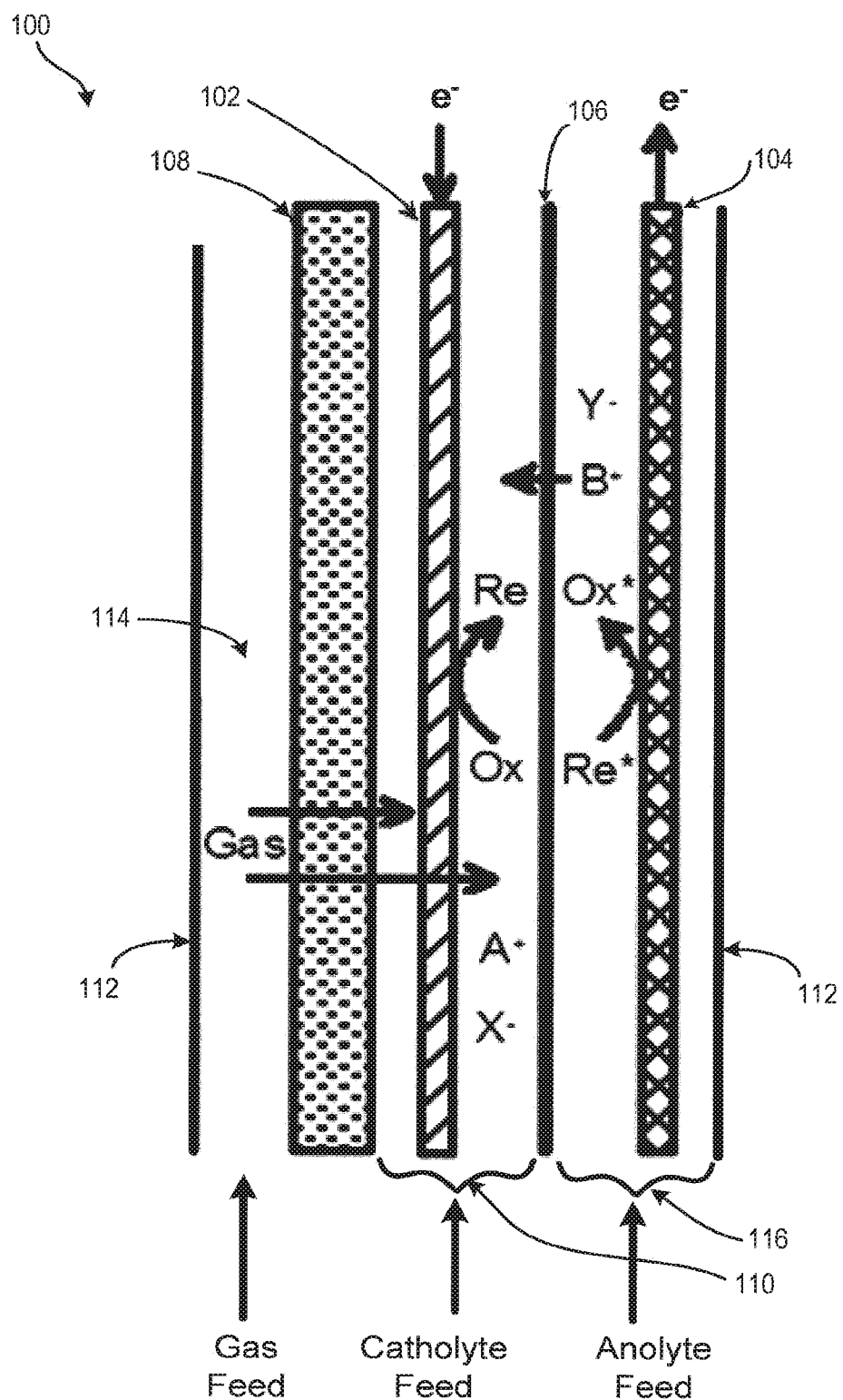
FIG. 1 depicts an electrochemical reactor according to embodiments disclosed herein.

With reference to FIG. 1, the basic structure of an electrochemical reactor 100 is shown. Electrochemical reactor 100 is designed and optimized for multi-phase cathodic processes requiring or benefiting from the combination of gaseous and liquid feedstocks. The reactor design minimizes capital costs and operating costs while remaining versatile for a variety of applications. The reactor utilizes relatively low-cost materials and components, is mechanically robust, compact, can be readily scaled up or down in size, operates with low voltage, and is easy to assemble and service. The reactor is compatible with a variety of input feeds and process conditions making it convenient to optimize for a variety of electrochemical processes.

Electrochemical reactor 100 includes one or more cathode 102, also known as the cathode electrode, and one or more anode 104, also known as an anode electrode, separated by an ion conducting or ion-permeable separator 106. Cathode 102 is connected to the negative pole and the anode 104 is connected to the positive pole of a direct current power supply (not shown). The electrochemical reactor further includes a gas distributor 108. Gas distributor 108 is positioned near or contacting cathode 102 such that a cathode chamber 110 is defined between gas distributor 108 and separator 106. Cathode chamber 110 confines cathode 102 such that gas and liquid-phase materials injected into cathode chamber 110 interact with the surface of the cathode 102. In an embodiment, electrochemical reactor 100 further includes a containment boundary 112 that houses cathode 102, anode 104, separator 106, gas distributor 108, and cathode chamber 110. Containment boundary 112 also serves to form a gas chamber 114 between containment boundary 112 and gas distributor 108 and an anode chamber 116 between the separator 106 and containment boundary 112.

In an embodiment, cathode 102 is porous and permeable to gas and liquid. In some embodiments, cathode 102 is a high porosity or high surface area material, and is continuously conductive down the length of its form. Any cathode material suitable for use in multiphase electrolysis reactions can be used. Exemplary cathode materials include, but are not limited to, pure metals, alloys, conductive polymers, and carbonized or graphitized polymers. Examples of porous material formats include sintered or bonded particles, sintered or bonded fibers, woven mesh, continuous fibers or filaments, cloths, felts, and electro-spun or melt-spun filamentous forms.

In some embodiments, cathode 102 may include a coating. Any coating that imparts a desirable property to cathode 102 can be used. For example, coatings that impart conductivity, reaction selectivity, catalysis, adsorption, resistance to hydrogen evolution, increased surface area, or modifying wettability can be used.

In an embodiment, the porosity and pore structure of cathode 102 can be uniform, graded or random. In some embodiments, a specific surface area greater than 10 $m^2$ per 1 $m^2$ superficial area of cathode 102 is preferred. In a preferred embodiment, the specific surface area is greater than 100 $m^2$ per 1 $m^2$ superficial area of cathode 102.

In an embodiment, cathode 102 may be positioned anywhere within cathode chamber 110, including having direct contact with separator 106 and/or gas distributor 108.

In a preferred embodiment, cathode 102 comprises continuous carbon fibers. In other embodiments, cathode 102 is a mass of sintered or bonded carbon fibers in a continuous form. In an embodiment, carbon fiber surfaces of cathode 102 are modified to possess carbon oxide species. Carbon oxide species can be introduced by thermal treatment in oxidizing atmosphere, wet chemical treatment with alkali or oxidizers, electrochemical treatment, sonochemical treatment, or a combination of such treatments. In some embodiments, the carbon fiber surfaces of cathode 102 are coated with a catalyst. Examples of catalysts include an organic material (e.g., adsorbed or bonded molecules or polymers) or an inorganic material (e.g., adsorbed, bonded or electrodeposited metals, semiconductors, alloys and their oxide or sulfide derivatives).

For a given superficial current density, a three-dimensional electrode will operate at lower specific current density than a two dimensional (planar) electrode, which is advantageous for electrochemical transformations requiring lower specific current densities to achieve high current efficiency for kinetically slow electrochemical processes, slow mass transport, or to minimize competing side reactions. In an embodiment, cathode 102 can be a three dimensional electrode possessing a large surface area throughout its macroscopic form. The superficial electrode surface of cathode 102 area is defined as the two-dimensional area of the macroscopic form, such as for a planar or tubular form. The three-dimensional specific surface area of cathode 102 includes structural, topographical, and porous features generally in the millimeter, micron, and nanometer size regimes. In an embodiment, cathode 102 comprises electrodes exhibiting electroactivity over the majority of their specific surface area. In an embodiment, a specific surface area greater than 10 $m^2$ per 1 $m^2$ superficial area of cathode 102 is preferred. In another embodiment, the specific surface area of cathode 102 is greater than 100 $m^2$ per 1 $m^2$ superficial area.

In an embodiment, cathode 102 may be in a planar or tubular form having planar parallel faces, corrugated faces or other shapes for enhancing flow dynamics and distribution of materials around and throughout cathode 102. In some embodiments, the cathode thickness may be between about 0.1 and 10 millimeters and preferably between about 0.5 and 5 millimeters. In an embodiment, cathode 102 thickness is between about 1 and 3 millimeters. In certain embodiments, the shape and dimensions of cathode 102 may be defined by cathode 102. In an embodiment, the shape and dimension of cathode 102 may be rigid or semi-rigid forms including bonded particles, bonded fibers, woven filaments, felts, structural foams, etc. In some embodiments, the shape and dimensions of cathode 102 are defined by the boundaries of the space in which cathode 102 is contained. In an embodiment, the shape and dimension of cathode 102 may be determined by soft forms including non-bonded particles or fibers. In an embodiment, cathode 102 has a tubular form with at least one non-planar face.

In an embodiment, anode 104 is porous and permeable to gas and liquid. Anode 104 may be comprised of any anode suitable for use in a multiphase electrolysis reaction.

In an embodiment, anode 104 is a dimensionally stable anode made from an expanded titanium mesh coated with a catalyst. The catalyst is optimized for oxidation of species in an anolyte solution filling anode chamber 116, such as water or halides or other redox active materials, at reduced overpotentials or voltage. In some embodiments, the catalyst is a precious metal, noble metal, platinum group metal or oxides of such metals. In a one embodiment, the catalyst is iridium oxide.

Anode 104 may be positioned anywhere within anode chamber 116, including having direct contact with separator 106.

In one embodiment, anode 104 may be a three-dimensional electrode. In an embodiment, anode 104 comprises electrodes exhibiting electroactivity over the majority of their specific surface area. In an embodiment, anode 104 has a specific surface area greater than 1 $m^2$ per 1 $m^2$ superficial area. In another embodiment, anode 104 has a specific surface area greater than 5 $m^2$ per 1 $m^2$ superficial area. In another embodiment, anode 104 has a specific surface area greater than 1 $m^2$ per 1 $m^2$. In another embodiment, anode 104 has a specific surface area greater than 10 $m^2$ per 1 $m^2$ superficial area.

In an embodiment, anode 104 may be in a planar or tubular form having planar parallel faces, corrugated faces, perforated faces, or other shapes for enhancing flow dynamics and distribution of materials around and throughout anode 104. In some embodiments, the thickness of anode 104 may be between about 0.1 and 10 millimeters. In another embodiment, the thickness of anode 104 may be between about 0.5 and 5 millimeters. In another embodiment, the thickness of anode 104 may be between about 1 and 2 millimeters.

In some embodiments, the shape and dimensions of anode 104 may be defined by anode 104. In an embodiment, the shape and dimensions of anode 104 may be rigid or semi-rigid forms including plate, expanded mesh, woven mesh, bonded or sintered fibers, felts, etc. In another embodiment, the shape and dimensions of anode 104 may be defined by anode 104 as a tubular form composed of an expanded mesh.

In an embodiment, separator 106 is ion permeable and allows for selective passage of ions between electrodes while hydraulically and electrically separating cathode chamber 110 and anode chamber 116. In an embodiment, separator 106 separates the catholyte and anolyte fluids and materials contained, respectively, within cathode chamber 110 and anode chamber 116, and thus provides control of two-phase fluid dynamics (flow distribution, mixing, electrode contact, partial pressures of gases), prevents undesirable side reactions, prevents electrode shorting or shunt losses, and allows for precise control of process conditions at each electrode.

In an embodiment, separator 106 may be a porous, microporous or nanoporous separator composed of materials including, but not limited to, polypropylene, polyethylene, polytetrafluoroethylene, polyvinylidine difluoride, polysulfone, polyethersulfone, or a ceramic material (e.g., alumina, zirconia, rare earth oxide, nitride). In an embodiment, separator 106 may be an ion exchanger, including cation exchange membranes (e.g., perfluorosulfonic acid, sulfonated polyfluorostyrene, sulfonated polystyrene-divinylbenzene, perfluorosulfonimide, and perfluoro carboxylate membranes) or anion exchange membranes (e.g., quaternary ammonium polystyrene-divinylbenzene and doped polybenzimidazole membranes). In an embodiment, separator 106 is a perfluorosulfonic acid membrane such as Nafion™.

In an embodiment, the resistance that separator 106 introduces between cathode 102 and anode 104 is minimized and the thickness of separator 106 is thick enough for mechanical integrity to resist hydraulic rupture, mechanical tearing, excessive deformation, and shorting or leaking through defects and pinholes. In an embodiment, separator 106 has a thickness of between about 50 and 150 microns for polymers and between about 1,000 and 4,000 microns for ceramics. In an embodiment, separator 106 may possess additional components for mechanical reinforcement such as polymer fibers or composite laminates.

In an embodiment, gas is dispersed over an area of cathode chamber 110 through gas distributor 108. In an embodiment, gas is dispersed over an area of cathode chamber 110 through gas distributor 108 that corresponds to the area of cathode chamber 110 that is exposed to gas distributor 108. Gas passes through gas distributor 108 by means of a pressure differential into cathode chamber 110. Gas entering the cathode chamber 110 mixes with and disperses into the catholyte and cathode 102 (in the forms of dissolved gas and gas bubbles) located in the cathode chamber 110. This creates turbulence in cathode chamber 110 and increases the space velocity of materials passing around cathode 102.

In an embodiment, gas distributor 108 is a porous or microporous material that allows gas to permeate through its wall and also resists water permeation. In an embodiment, gas distributor 108 may contain a tube that is a non-conductive, hydrophobic material, such as polyethylene, polypropylene, polytetrafluoroethylene, or polyvinylidene difluoride. In another embodiment, gas distributor 108 may be a microporous ceramic such as alumina, zirconia, titania or other suitable material with a hydrophobic coating.

In an embodiment, the pore diameter rating for gas distributor 108 is less than about 10 microns. In another embodiment, the pore diameter rating for gas distributor 108 is less than or equal to about 5 microns. The pores of gas distributor 108 may be masked in part to bias the gas permeation through regions of gas distributor 108 for purposes including making the ends of gas distributor 108 gas and liquid impermeable in the catholyte manifold and current collector regions, compensation for pressure gradients, gas loading in the catholyte, or residence time in cathode chamber 110.

The thickness of gas distributor 108 may be chosen to provide mechanical rigidity as a cathode chamber boundary and optionally serve as a cathode support. In an embodiment, the thickness of gas distributor 108 may range between about 1 and about 10 millimeters. In an embodiment, the thickness of gas distributor 108 is about 6 millimeters.

In some embodiments, at least one face of gas distributor 108 is oriented parallel to the face of separator 106. A pressure differential from gas chamber 114 at higher pressure to cathode chamber 110 at lower pressure may be used to transport gas through the gas distributor. A pressure differential, which is greater than the sum of the flow resistance of the gas distributor pores and the hydraulic pressure in cathode chamber 110, can be used to promote even gas distribution. In an embodiment, the pressure differential may be between about 0.5 and 15 psig. In another embodiment, the pressure differential may be between about 0.5 and 5 psig. The flow rate of gas through gas distributor 108 is dependent on the pressure differential, the flow resistance of the gas distributor pores, and the hydraulic pressure in cathode chamber 110. In some embodiments, the flow rate of gas through gas distributor 108 ranges between about 3 to about 70 milliliters per minute per square centimeter of gas distributor 108 surface area exposed to cathode chamber 110. In some embodiments, the flow rate of air is about 40-50 milliliters per minute per square centimeter of gas distributor 108 surface area exposed to cathode chamber 110.

In an embodiment, the dimensions of cathode chamber 110 approximately match the thickness and superficial area of cathode 102. In an embodiment, cathode chamber 110 may be an open channel containing cathode 102 and through which the catholyte feed flows. In another embodiment, cathode chamber 110 may be a partitioned channel containing cathode 102 and also containing spacers, screens or other structures, which are positioned to maintain a uniform cathode chamber thickness and assist with fluid distribution and flow.

In an embodiment, containment boundary 112 may serve as an outer housing to the other components of electrochemical reactor 100. Containment boundary 112 can be made from structural thermoplastics (pure and filled) including, but not limited to, polyvinyl chloride (PVC), chlorinated polyvinylchloride (CPVC), polyvinylidine difluoride (PVDF), polyethylene, polytetrafluoroethylene (PTFE), ethylene tetrafluoroethylene (ETFE), acrylonitrile butadiene styrene (ABS) polymer blends, etc.

In an embodiment, the area dimensions of anode chamber 116 may be determined by the superficial area dimensions of anode 104. For the case of planar electrodes mounted in a plate and frame housing configuration, the thickness of anode chamber 116 is at least the thickness of anode 104 and must provide enough void space to allow liquid and gas to pass around anode 104. Alternatively, for the case of non-planar or tubular electrodes, the thickness of anode chamber 116 is determined, in part, by the size of the containment vessel. In the alternative case, anode chamber 116 may be an open reservoir for fluid around the anode. Anode chamber volume may be reduced to define a narrower flow channel around the anode 116 by filling the excess void space with a solid material such as that used for the containment vessel. Alternatively, the excess void space may contain baffles, partitions or a heat exchange coil.

Another embodiment of the electrochemical reactor described above is illustrated in FIGS. 2A and 2B, wherein electrochemical reactor 200 has a general tubular or annular configuration. The housing for electrochemical reactor 200 has three distinct parts an anode housing 220, a seat plate 234, and an end plate 236, each of which may be fabricated in quantity from structural thermoplastics (pure and filled) including, but not limited to, polyvinyl chloride (PVC), chlorinated polyvinylchloride (CPVC), polyvinylidine difluoride (PVDF), polyethylene, polytetrafluoroethylene (PTFE), ethylene tetrafluoroethylene (ETFE), acrylonitrile butadiene styrene (ABS) polymer blends, etc.

In an embodiment, anode housing 220 is an extruded tube, such as a standard schedule 80 pipe that is modified with tube fittings, feed-throughs, O-ring, or gasket sealing surfaces and threaded bolt holes. In an embodiment, anode housing 220 contains the anolyte solution within electrochemical reactor 200. In an embodiment, anode housing 220 contains the anolyte solution within an anolyte chamber 218. In an embodiment, anode housing 220 provides structural integrity to electrochemical reactor 200 and is what seat plate 234 and end plate 236 are fastened to, thereby holding electrochemical reactor 200 and its contents together as a single unit. In some embodiments, anode housing 220 is made from PVC.

In an embodiment, seat plate 234 contains a central opening with a tapered surface on which a separator 214 is sealed. A cathode 212 extends through seat plate 234. A cathode current distributor and compression ferrule 230 contacts cathode 212 and anchors it in place while simultaneously compressing separator 214 to make a gas-tight seal between a cathode flow channel 210 and the anolyte chamber 218. Seat plate 234 also has gasket or O-ring sealing surfaces for making gas-tight seals with anode housing 220 and with cathode current distributor and compression ferrule assembly 230.

In an embodiment, cathode current distributor and compression ferrule 230 may be constructed of a rigid material that is conductive and non-corrosive such as stainless steel alloys, high nickel alloys, and high purity titanium, for example. In an embodiment, cathode current distributor and compression ferrule 230 is 316 stainless steel. In yet another embodiment, the surfaces of current distributor and compression ferrule 230 facing into cathode flow channel 210 and manifold are masked with a non-conductive material such as a thermoplastic, a polymer coating, or an elastomeric adhesive coating.

In an embodiment, end plate 236 provides a gas inlet 202 and catholyte fluid distribution manifolds which are accessed through the catholyte inlet or outlet 208. In an embodiment end plate 236 seals against the end of a gas distributor tube 206 creating a separate gas chamber 204 down the center axis of electrochemical reactor 200. End plate 236 contains gasket and O-ring sealing surfaces for making gas-tight seals with gas distributor tube 206 and cathode current distributor and compression ferrule assembly 230. In an embodiment, end plate 236 provides the compressive force to seal separator 214 to seat plate 234, seal seat plate 234 to anode housing 220, seal the faces of the cathode current distributor and compression ferrule assembly 230 to end plate 236 and seat plate 234, seal gas distributor tube 206 and fasten electrochemical reactor 200 together.

In an embodiment, end plate 236 holds the cathode electrical feed-through posts 232, which contact cathode current distributor and compression ferrule 230 and are connected by means of conductors to the negative pole (direct current, DC) or ground (alternating current, AC) of a power supply. In one embodiment, electrical feed-through posts 232 are made from a material that is conductive and non-corrosive such as stainless steel alloys, high nickel alloys, and high purity titanium, for example. In an embodiment, cathode electrical feed-through posts 232 are 18-8 stainless steel.

As discussed above with respect to FIG. 1 and gas distributor 108, gas distribution tube 206 is a porous or microporous material that allows gas to permeate through its wall and resists water permeation. In an embodiment, gas distribution tube 206 is a non-conductive, hydrophobic material such as polyethylene, polypropylene, polytetrafluoroethylene, or polyvinylidene difluoride, for example. In an embodiment, gas distribution tube 206 may be a microporous ceramic such as alumina, zirconia, titania or other suitable material with a hydrophobic coating. Gas distribution tube 206 may be made by casting-sintering or extrusion production methods, for example. In an embodiment, gas distribution tube 206 contains pores having a diameter rating that is less than about 10 microns. In an embodiment, gas distribution tube 206 contains pores having a diameter rating that is less than about or equal to 5 microns. The pores of gas distribution tube 206 may be masked in part to bias the gas permeation through regions of gas distribution tube 206 for purposes including making the ends gas and liquid impermeable in the catholyte manifold and current collector regions, compensating for pressure gradients, gas loading in the catholyte, and/or modulating residence time in the cathode flow chamber.

In an embodiment, cathode flow channel 210 is defined by gas distribution tube 206 and separator 214. Cathode 212 resides within cathode flow channel 210 immersed in the catholyte liquid while gas is supplied from the back side of cathode 212 and the front side of cathode 212 faces the separator 214. Cathode 212 may be positioned anywhere within cathode flow channel 210, including having direct contact with the separator 214 and/or gas distribution tube 206.

As discussed above with respect to FIG. 1 and separator 106, separator 214 separates the catholyte and anolyte fluids from one another, thereby keeping the respective reactants and products from mixing in an uncontrolled manner, providing control of two-phase fluid dynamics (flow distribution, mixing, electrode contact, partial pressures of gases), preventing undesirable side reactions, preventing electrode shorting or shunt losses, and allowing for precise control of process conditions at each electrode. In an embodiment separator 214 may be a porous, microporous or nanoporous separator composed of materials including polypropylene, polyethylene, polytetrafluoroethylene, polyvinylidine difluoride, polysulfone, polyethersulfone or a ceramic material (e.g., alumina, zirconia, rare earth oxide, nitride). In an embodiment, separator 214 may be an ion exchange including cation exchange membranes (e.g., perfluorosulfonic acid, sulfonated polyfluorostyrene, sulfonated polystyrene-divinylbenzene, perfluorosulfonimide, and perfluoro carboxylate membranes) or anion exchange membranes (e.g., quaternary ammonium polystyrene-divinylbenzene and doped polybenzimidazole membranes), for example. Separator 214 may be formed into a tubular shape by casting, extrusion, or rolling flat sheets and bonding a seam. In an embodiment, separator 214 is a tubular perfluorosulfonic acid membrane such as Nafion™.

As discussed above with respect to FIG. 1 and cathode 102, in an embodiment, cathode 212, also known as a cathode electrode, is a high porosity or high surface area material that can conform to a tubular shape and be continuously conductive down the length of its form. Cathode 212 may be a pure metal, an alloy, a conductive polymer, a carbonized or graphitized polymer. In an embodiment cathode 212 has a coating that imparts conductivity, reaction selectivity, catalysis, adsorption, resistance to hydrogen evolution, increased surface area or modifies wettability. In an embodiment, cathode 212 may be made of one or more porous material formats including sintered or bonded particles, sintered or bonded fibers, woven mesh, continuous fibers or filaments, cloths, felts, and electro-spun or melt-spun filamentous forms. In an embodiment the electrode porosity and pore structure of cathode 212 may be uniform, graded or random. In an embodiment cathode 212 has an electrode specific surface area greater than about 10 $m^2$ per 1 $m^2$ superficial area. In an embodiment cathode 212 has an electrode specific surface area greater than about 100 $m^2$ per 1 $m^2$ superficial area. In an embodiment cathode 212 is continuous carbon fibers. The carbon fiber surfaces cathode 212 may be modified to possess carbon oxide species. In another embodiment, the carbon fiber surfaces of cathode 212 are coated with a catalyst that may be an organic material (e.g., adsorbed or bonded molecules or polymers) or an inorganic material (e.g., adsorbed, bonded or electrodeposited metals, semiconductors, alloys and their oxide or sulfide derivatives) or a mixture thereof.

As discussed above with respect to FIG. 1 and anode 104, the anode 216, also known as an anode electrode, can be a dimensionally stable anode consisting of an expanded titanium mesh coated with a catalyst. The catalyst is optimized for oxidation of species in an anolyte solution filling anolyte chamber 218, such as water or halides or other redox active materials, at reduced overpotentials or voltage. In some embodiments, the catalyst is a precious metal, noble metal, platinum group metal or oxides of such metals. In an embodiment, the catalyst is iridium oxide.

In an embodiment, anode 216 is in a tubular form, and may be in direct contact with separator 214, and may provide mechanical support to separator 214. In an embodiment, at least one titanium anode current collector tab 226 is affixed to the side of anode 216 and provides a point of attachment for the anode electrical feed-through post 228, which is also titanium.

Figure 2A:
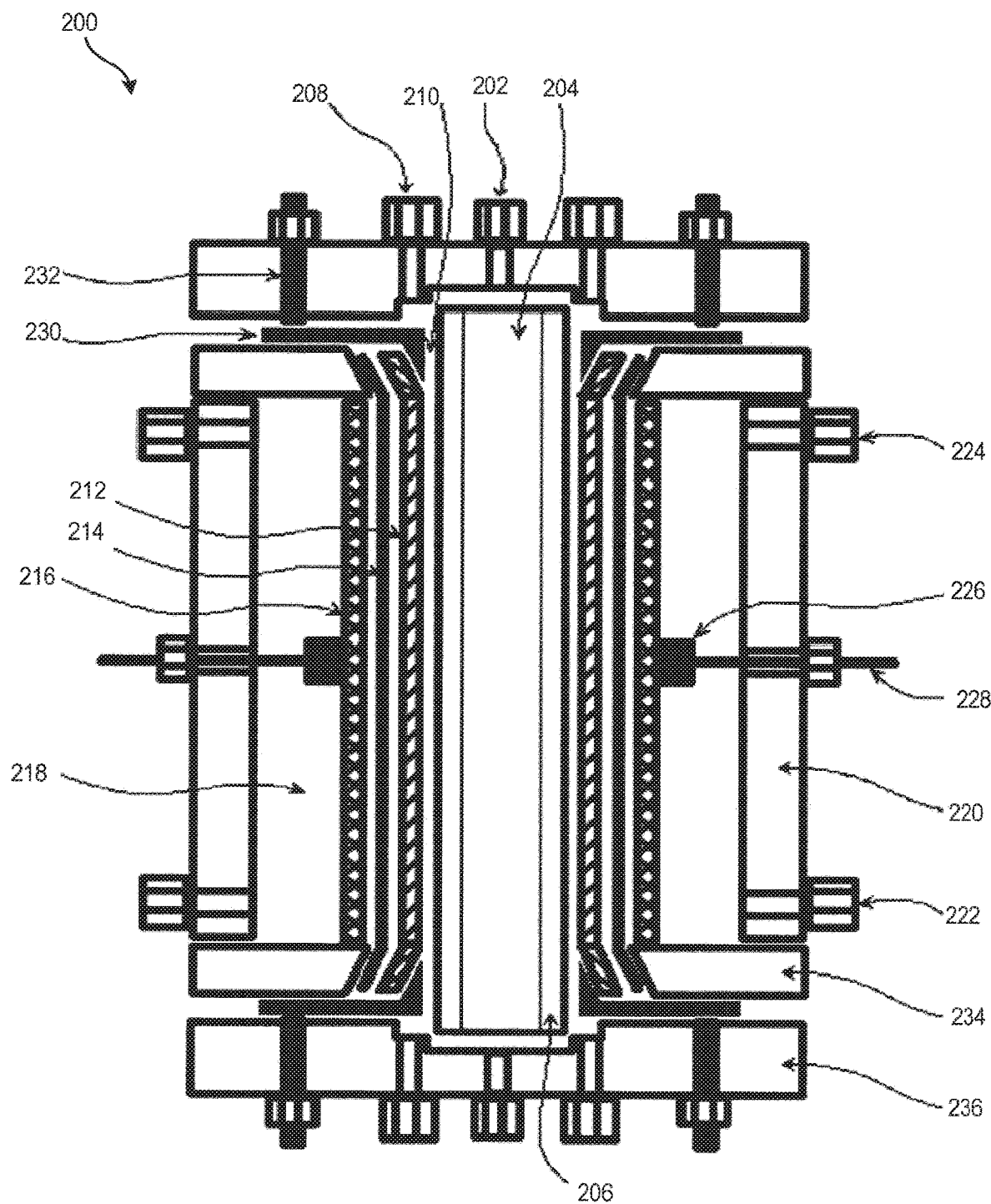
FIG. 2A depicts a cross-sectional view of the general configuration and components of an electrochemical reactor according to embodiments disclosed herein.
Figure 2B:
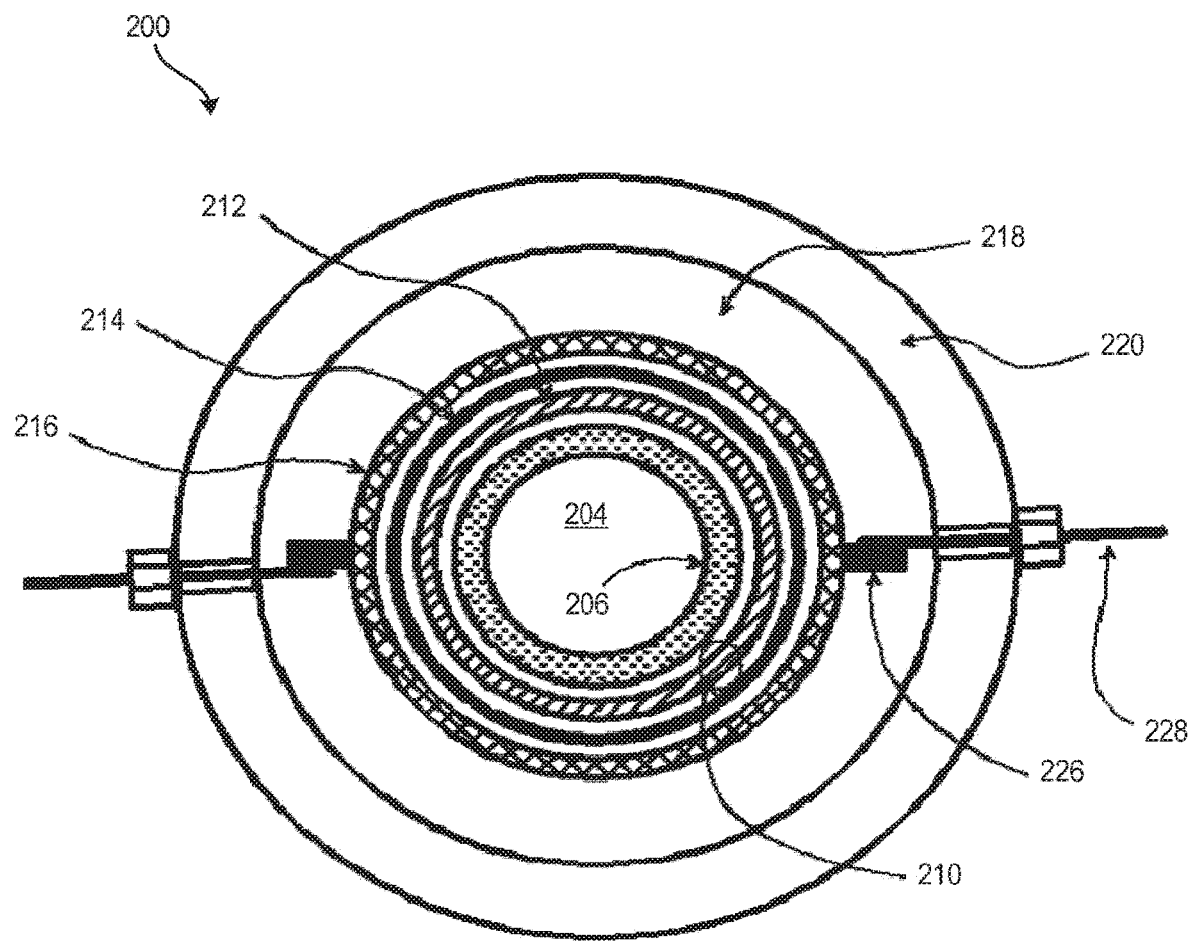
FIG. 2B depicts an end-on view of the concentric elements in the mid-section of an electrochemical reactor according to embodiments disclosed herein.

In one embodiment, a heat transfer coil, which is not depicted in FIG. 2A or FIG. 2B, can be positioned in anolyte chamber 218 with feedthroughs using two of the anolyte inlet and outlet/vent ports 222 and 224, respectively. If required, the heat transfer coil may be used in the reactor process for cooling or heating the anolyte solution. In an embodiment, the heat transfer coil is a metal or plastic tube made of a non-corrosive material such as stainless steel alloys, high purity titanium, high nickel alloys, polyvinyl chloride, polypropylene, polyvinylidene difluoride, polytetrafluoroethylene. The heat transfer fluid circulated through the coil may be water, catholyte solution, gas, air, glycol solutions, for example.

A tubular or concentric reactor housing design requires significantly less material in the reactor vessel to accommodate elevated internal pressures than that of a planar stacked design (e.g., plate and frame design). There are also significantly fewer fasteners and/or compression devices required for holding a tubular assembly together than those required to hold a planar stack together. There is also a significant reduction in sealing area and potential for leaks in the tubular reactor relative to a planar stack reactor design.

Electrochemical Reactor Systems

Figure 3A:
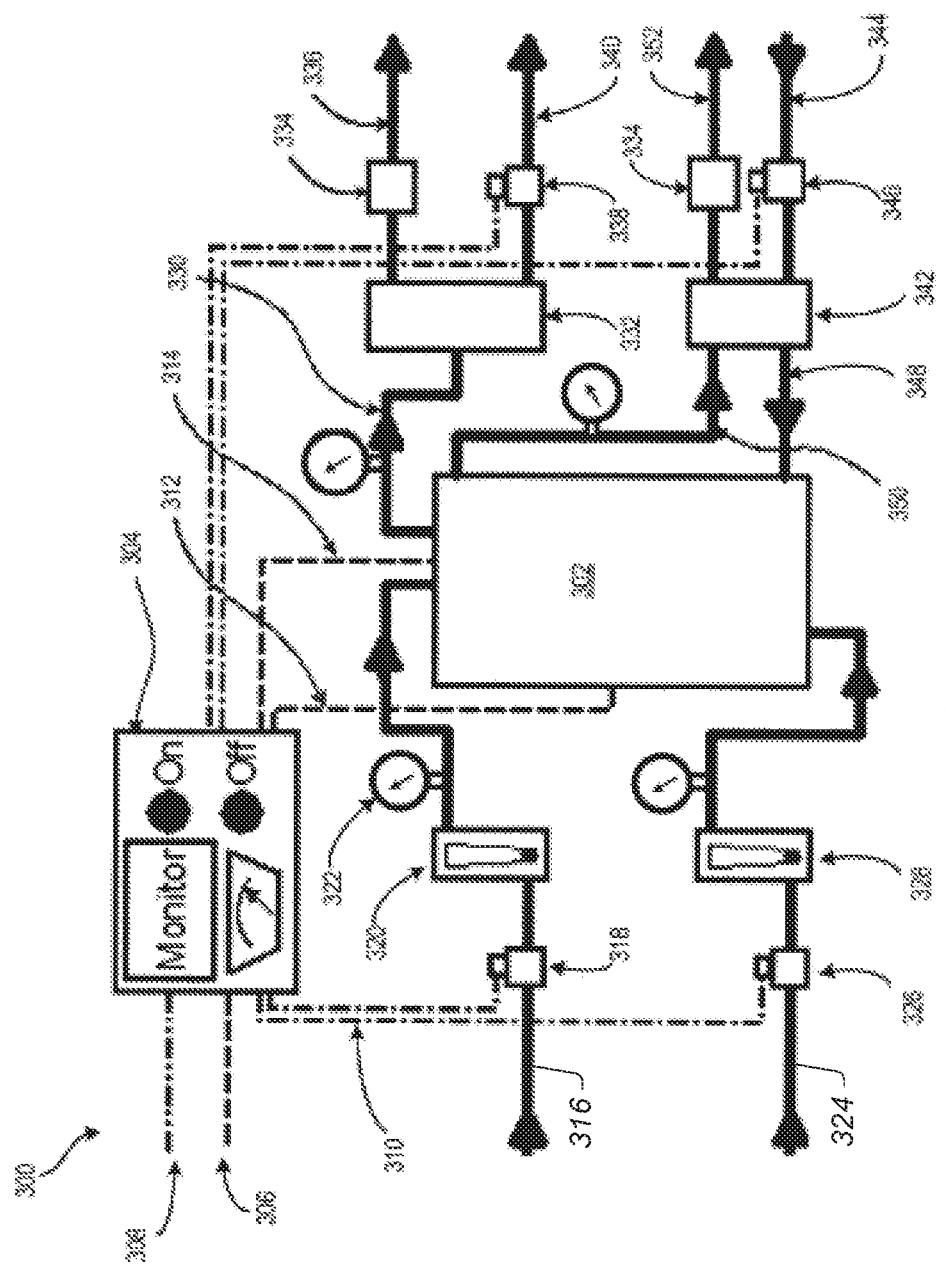
FIG. 3A depicts one example of a flow pathway configuration for an electrochemical reactor system with a closed anolyte loop according to embodiments disclosed herein.

FIG. 3A depicts an embodiment of the basic process flow, also referred to as the flow pathway, of a reactor system 300 that incorporates an embodiment of electrochemical reactor 100 as depicted in FIG. 1. Embodiments of reactor system 300 are determined by the particular processes and applications of interest. The electrochemical reactor 302 is a schematic representation of electrochemical reactor 100 as described above and depicted in FIG. 1. In an embodiment of reactor system 300, the system controller 304 contains a variety of components that allow the system to be operated by push button activation and remote control. System controller 304 may possess on-board system status readouts, indicators, monitors or other user-interface features. The controller may possess a central processing unit or process logic controller providing capabilities such as data logging, system monitors, equipment control loops and automated operation algorithms. The system controller has a main power input 306 for line power and can be alternating current or direct current power. The external monitor and control link 308 may be a wired or wireless connection to a communications and data transfer network providing a means of controlling the reactor system and monitoring its status from a remote location.

In an embodiment, system controller 304 has flow control valve control loops 310 for controlling the flow control valves 318, 326, 338 and 346 which, in turn, control the flow of materials into and out of reactor system 300. Other standard sensing and feedback loops can be integrated with system controller 304 and other system components such as pressure, temperature, flow rate, totalizers, liquid level, oxidation reduction potential (ORP), pH, conductivity, gas sensors, ion selective electrodes and other sensors and controls specialized for a particular application.

In an embodiment, system controller 304 contains a power supply, not depicted in FIG. 3A, that provides electrical power to electrochemical reactor 302. The power supply is connected to electrochemical reactor 302 by means of electrical conductors. When direct current is employed, the positive pole of the power supply is connected by means of the anode power lead 312 to the anode electrical feed-through posts (not depicted in FIG. 3, but an embodiment of which is described above and depicted in FIGS. 2A and 2B as anode electrical feed-through post 228) while the negative pole of the power supply is connected my means of the cathode power lead 314 to the cathode electrical feed-through posts 232 not shown in FIG. 3A, an embodiment of which is described above and depicted in FIGS. 2A and 2B as cathode electrical feed-through post 232. Both poles of the direct current power supply may be floating potentials (not grounded), or either pole may be grounded while the other has a floating potential. The power supply may provide voltage control and allow the current to float or the power supply may provide current control and allow the voltage to float. Alternatively, either pole of the power supply may be potentiostatically controlled relative to a reference electrode potential.

In an embodiment of reactor system 300, gas is fed into the electrochemical reactor 302 through the gas feed line 316, passes through gas flow control valve 318 then passes through a gas flow meter 320 and into a gas inlet (not depicted in FIG. 3A, but described above and depicted in FIGS. 2A and 2B as gas inlet 202) of electrochemical reactor 302. A pressure indicator 322 is positioned just upstream of the reactor to measure the inlet pressure of the gas feed.

In an embodiment of reactor system 300, liquid catholyte feed solution is fed into electrochemical reactor 302 through the catholyte feed line 324, passes through catholyte flow control valve 326 then passes through a catholyte flow meter 328 and into one pair of catholyte inlets or outlets (not depicted in FIG. 3A, but described above and depicted in FIG. 2A as catholyte inlet or outlet 208) at one end of electrochemical reactor 302. A pressure indicator is positioned just upstream of electrochemical reactor 302 to measure the inlet pressure of the catholyte feed solution.

The gas feed and catholyte feed solution combine as a process fluid inside the cathode flow channel (not depicted in FIG. 3A, but described above and depicted in FIGS. 2A and 2B as catholyte flow channel 210) and exit the reactor together through the pair of catholyte inlets or outlets (not depicted in FIG. 3A, but described above and depicted in FIG. 2A as catholyte inlet or outlet 208) at the opposite end of the reactor to the catholyte feed. The cathode process fluid output line 330 enters a gas-liquid separator 332 where the gas-phase materials are separated from the liquid-phase materials. A pressure indicator is positioned just downstream of electrochemical reactor 302 to measure the outlet pressure. Gas-phase materials exit through the gas vent and gas-phase product outlet 336. A back pressure regulator 334 may be added to the gas vent to create an elevated pressure within the reactor. The liquid component of the cathode process fluid captured in the gas-liquid separator exits through the liquid and liquid-phase product outlet 340. Liquid product flow control valve 338 may be used for dispensing or allowing for the use of a back pressure regulator on the gas vent.

Anolyte solution or makeup water is fed to the anolyte reservoir 342 through the anolyte reservoir feed line 344. Anolyte reservoir feed flow control valve 346 controls when anolyte solution or makeup water is added to the reservoir. Anolyte reservoir 342 serves to hold an amount of anolyte solution that maintains a constant liquid level in the anolyte chamber (not depicted in FIG. 3A, but described above and depicted in FIGS. 2A and 2B as anolyte chamber 218). Anolyte reservoir 342 may be positioned such that anolyte solution transfers from the reservoir to the anolyte chamber, by means of gravity, through the anolyte chamber inlet line 348, which is connected to the anolyte inlet (not depicted in FIG. 3A, but described above and depicted in FIG. 2A as anolyte inlet 222). An anolyte chamber outlet and gas vent line 350 connects the anolyte outlet and gas vent (not depicted in FIG. 3, but an embodiment of which is described above and depicted in FIG. 2A as outlet vent port 224) to the anolyte chamber to allow any gas evolved at the anode to exit or, alternatively to allow the anolyte to be circulated through the anolyte chamber by means of a pump or pressure differential between the anolyte inlet and outlet and gas vent.

The anolyte reservoir gas vent line 352 allows gas that has accumulated in anolyte reservoir 342 to exit the system. The gas may pass through back pressure regulator 334 that serves to regulate and maintain pressure of the anolyte in the reactor system.

Figure 3B:
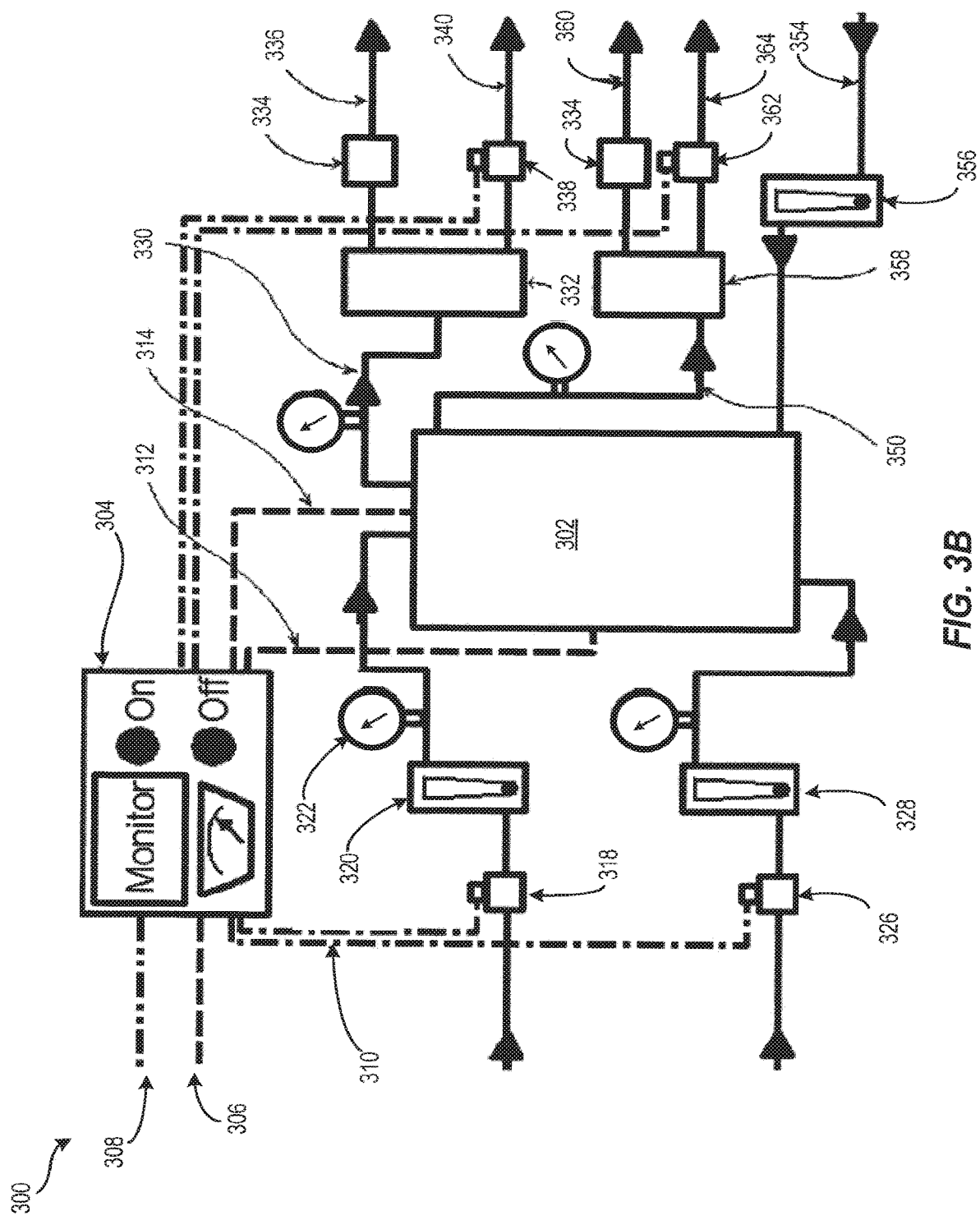
FIG. 3B depicts another example of a flow pathway configuration for an electrochemical reactor system with a pass-through anolyte according to embodiments disclosed herein.

FIG. 3B depicts another embodiment of reactor system 300 depicting an embodiment of the flow pathway where the anolyte passes through the anode chamber of the reactor once and the anolyte output is collected. Anolyte solution is supplied through the anolyte feed line 354, passes through an anolyte flow meter 356 and enters the anolyte chamber. Anolyte exits the anolyte chamber through anolyte chamber outlet and gas vent line 350 into the anolyte liquid-gas separator 358. The anolyte gas vent line 360 allows gas that has accumulated in the anolyte liquid-gas separator to exit the system. The gas may pass through back pressure regulator 334 that serves to regulate and maintain pressure of the anolyte in the reactor system. The anolyte captured in the gas-liquid separator exits through the anolyte outlet line 364. An anolyte liquid flow control valve 362 may be used for dispensing or allowing for the use of a back pressure regulator on the gas vent.

Figure 4:
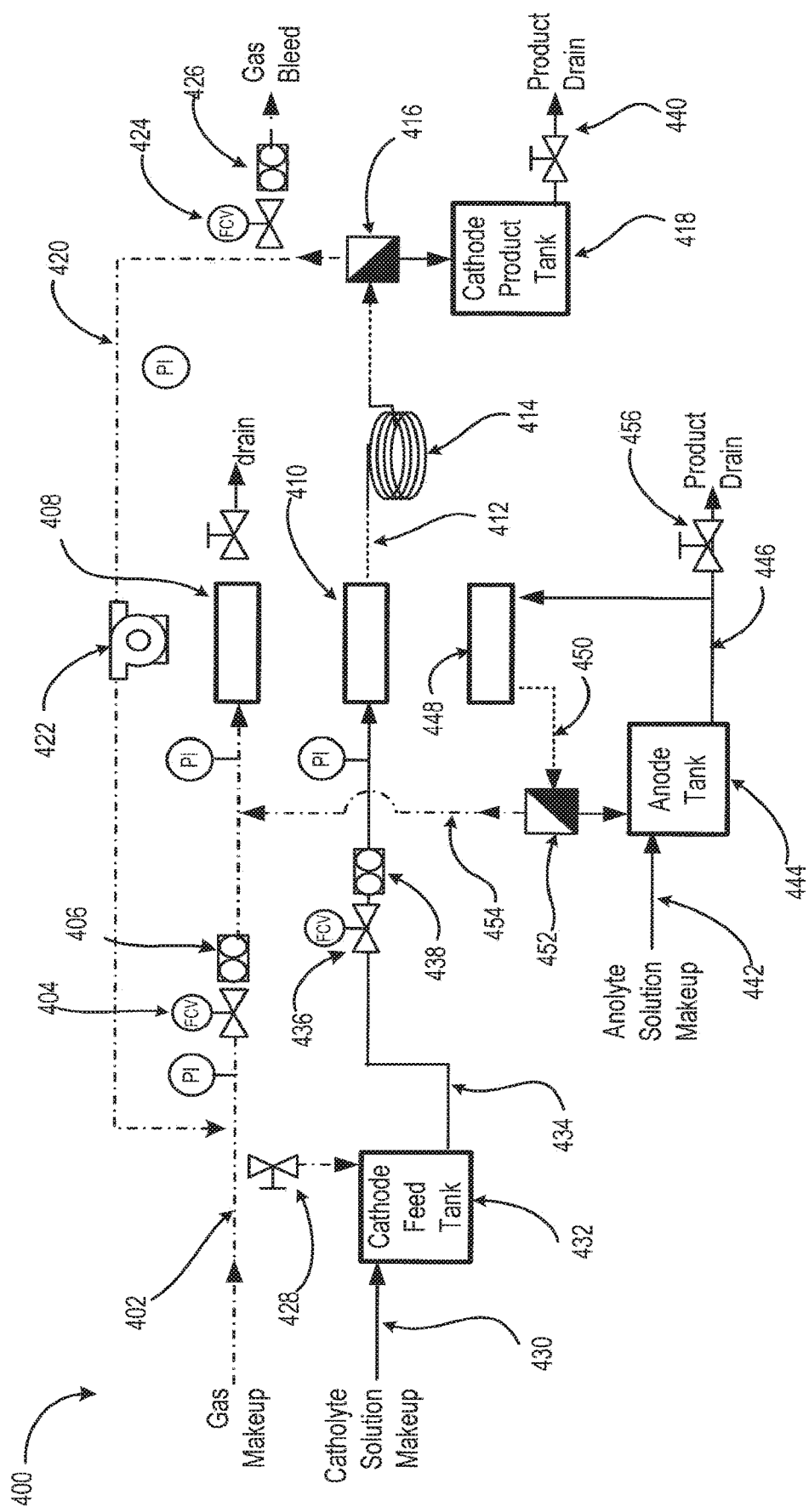
FIG. 4 depicts a fluid process flow diagram according to embodiments disclosed herein.

FIG. 4 depicts an embodiment of a reactor system 400 that has a reactor system fluid process flow, also known as a flow pathway, that enables gas recirculation within reactor system 400. A regulated gas makeup stream enters the gas circulation loop through the gas inlet line 402. The gas passes through the gas feed flow control valve 404 and the gas feed flow meter 406 and then enters the gas chamber 408 of the reactor. At least one boundary of the gas chamber is a gas distributor (not depicted in FIG. 4, but described above and depicted in FIG. 1 as gas distributor 108). The gas passes through the gas distributor and into the cathode chamber 410. Excess gas not consumed in electrochemical process exits cathode chamber 410 co-linearly with liquid catholyte and cathodic products formed through the cathode product line 412. The liquid and gas mixture passes through a cooling coil 414 prior to entering a gas-liquid separator 416. The separated liquid, which can contain products formed in cathode chamber 410, is collected in a cathode product tank 418. The separated gas flows through a gas recirculation line 420, through a gas pump 422 and is returned to gas inlet line 402. A portion of the separated gas is removed from the system through a gas bleed flow control valve 424 and a gas bleed flow meter 426. Bleed rate of gas from the system is preferably the same as the mass flow of the gas makeup stream entering the system less the mass consumption of gas in the reactor less the mass production of gas recovered from the anode chamber 448 and added to the gas makeup stream through an anode gas vent 454.

While gas is passing through the system described in reference to FIG. 4, a catholyte solution makeup 430 is added to the cathode feed tank 432 where the head space of the tank can be open to the gas makeup stream through a gas pressure line 428. In some embodiments, the pneumatic pressure for the gas makeup stream may be used to feed the catholyte solution into cathode chamber 410 of the reactor. In additional embodiments, the hydraulic pressure of the catholyte solution makeup may be used to feed the catholyte solution into cathode chamber 410 of the reactor. The catholyte flows from cathode feed tank 432 through the catholyte inlet line 434, passes through a catholyte flow control valve 436 and catholyte flow meter 438 and enters cathode chamber 410 of the reactor. Excess liquid catholyte not consumed in electrochemical process and cathodic products formed exit cathode chamber 410 co-linearly with gas through cathode product line 412. The liquid and gas mixture passes through cooling coil 414 prior to entering gas-liquid separator 416. The separated liquid, which can contain products formed in cathode chamber 410, is collected in cathode product tank 418. The liquid cathode product can be removed from the system during or after operation through the cathode product drain 440.

While gas and catholyte is passing through the system described in reference to FIG. 4 an anolyte solution makeup 442 is added to the anode feed tank 444. The anolyte is supplied through anolyte feed line 446 to the anode chamber 448 by the action of gravity or a pump (not shown). Excess liquid anolyte not consumed in electrochemical process and anodic products formed, including gas, exit the anode chamber collinearly through the anode product line 450 and then pass through a gas-liquid separator 452. The separated liquid is returned to anode feed tank 444 while the separated gas is optionally fed to the gas makeup stream through anode gas vent 454. Anode gas vent 454 also serves to expose anode chamber 448 to the gas inlet line pressure such that the differential pressure between anode chamber 448 and cathode chamber 410 remains constant at any gas inlet line pressure or during pressure fluctuations in the system. The liquid anode or anode product can be removed from the system during or after operation through the anode product drain 456. While gas, catholyte, and anolyte are passing through the system described in reference to FIG. 4 a voltage or current is applied to the reactor by a controller which is an embodiment of controller 304 described above and depicted in FIGS. 3A and 3B.

METHODS OF USE

In some embodiments, a method of carrying out a multiphase electrochemical process uses embodiments of the electrochemical reactors described above in order to promote efficient and productive electrochemical transformation of material. The method generally begins by providing a cathode chamber having a cathode disposed therein and an anode chamber having an anode disposed therein. The cathode chamber and anode chamber share a common boundary, with the common boundary being an ion-permeable separator. The boundary of the cathode chamber opposite the ion-permeable separator is a gas distributor (i.e., the cathode in the cathode chamber is disposed between the ion-permeable separator and the gas distributor). In a subsequent step, the cathode chamber is flooded with a catholyte and the anode chamber is flooded with an anolyte. In some embodiments, the catholyte and anolyte include species that can participate in the electrochemical reaction. In a subsequent step, a gas phase is injected into the cathode chamber through the gas distributor. A voltage or current is then applied to the cathode and anode, and the electrochemical reaction proceeds.

The cathode chamber and anode chamber provided in the initial step can be similar or identical to the cathode and anode chambers described in greater detail above. In some embodiments, providing the cathode and anode chambers will entail providing an electrochemical reactor as described above, including the annular or tubular electrochemical reactor described above.

In the next step, the cathode and anode chambers are flooded with catholyte and anolyte, respectively. Flooding of the chambers can generally include occupying up to 90% of the void space of the catholyte chamber with catholyte or up to 100% of the void space of the anolyte chamber with anolyte. Flooding of the chambers can be carried out by using, for example, catholyte inlet 208 and anolyte inlet 222 as depicted in FIG. 2A.

The catholyte used to flood the catholyte chamber is composed of at least one liquid, such as liquid water, which can serve as a carrier medium, a transport medium and optionally a participant in an electrochemical process at the cathode. Referring to FIG. 1, the catholyte may contain electrochemically active species ("Ox") which can accept at least one electron ($e^-$) and be reduced to an electrochemical product or products ("Re") at or near the cathode surface. The catholyte may contain ionic species, "$A^+$" and "$X^-$," where "$A^+$" generally denotes a positively charged species including, but not limited to protons, deuterons, lithium, sodium, potassium, magnesium, calcium, quaternary amines or a product or byproduct of the electrochemical process. "$X^-$" generally denotes a negatively charged species including, but not limited to fluoride, chloride, bromide, iodide, carbonate, bicarbonate, sulfate, bisulfate, phosphate, orthophosphate, hydroxide, peroxide anion, anions of carboxylic acids (e.g., methyl acetate, citrate, hexanoate, salicylic acid, ethylenediaminetetraacetate, oxalate), borates, aluminates or a product or byproduct of the electrochemical process. The catholyte may additionally contain chemically active species which can participate in an electrochemical reduction process or react with reduction products as they are formed and cause a transformation or produce a reaction product as a result of such chemical transformation. The catholyte may additionally contain electrolytes, salt, acid, alkali, organic materials, surfactants, colloids, emulsions, nanoparticles, and catalysts.

The anolyte is composed of at least one liquid, such as liquid water, which can serve as a carrier medium, a transport medium and optionally a participant in an electrochemical process at the anode. The anolyte may contain electrochemically active species ("Re*") which can liberate at least one electron ($e^-$) and be oxidized to an electrochemical product or products ("Ox*") at or near the anode surface. The anolyte may contain ionic species, "$B^+$" and "$Y^-$," where these species may be different than $A^+$" and "$X^-$," but may also be the same. "$B^+$" generally denotes a positively charged species including, but not limited to protons, deuterons, lithium, sodium, potassium, magnesium, calcium, quaternary amines or a product or byproduct of the electrochemical process. "$Y^-$" generally denotes a negatively charged species including, but not limited to fluoride, chloride, bromide, iodide, carbonate, bicarbonate, sulfate, bisulfate, phosphate, orthophosphate, hydroxide, peroxide anion, borates, aluminates or a product or byproduct of the electrochemical process. The anolyte may additionally contain chemically active species which can participate in an electrochemical oxidation process or react with reduction products as they are formed. The catholyte may additionally contain electrolytes, salt, acid, alkali, organic materials, surfactants, colloids, emulsions, nanoparticles, and catalysts.

Once the cathode chamber and anode chamber arc flooded with catholyte and anolyte, respectively, the next step involves injecting gas into the cathode chamber through the gas distributor. The gas phase material is dispersed through the entire face of the electrode where it may interact with the electrode surface and interior and contact the catholyte and be entrained within the liquid phase in the cathode flow path.

The gas fed into the gas chamber is composed of at least one material in the gas phase. The gas may contain electrochemically inert materials such as nitrogen ($N_2$), helium, neon, argon, krypton, and xenon. The gas may contain electrochemically and thermochemically reactive materials including examples such as hydrogen, oxygen ($O_2$), chlorine ($O_2$), nitrous oxides (e.g., $N_2O$, $NO$, $NO_2$), ozone ($O_3$), and carbon dioxide ($CO_2$). The gas may contain a single component or a mixture of components including combinations of inert and reactive components including mixtures such as air. The origin of gas and its components, in part or in their entirety, can include gas evolved by anodic processes in the anode chamber and gas exiting the cathode chamber to be recycled back into the electrochemical process. Alternatively, the origin of gas and its components, in part or in their entirety, may be external to the reactor and supplied to the reactor by various means, including a compressor, blower, pump, exhaust manifold, compressed gas tank, evaporate from a cryogenic liquid source, and pressure swing absorption gas separator. A combination of sources may be desirable depending on the particular application.

As noted above, the gas phase is injected into the cathode chamber via the gas distributor. The gas distributor can disperse gas over the entire area of the cathode chamber exposed to the distributor, and consequently, over the entire face of the flooded cathode. The gas passes through the gas distributor by means of a pressure differential into the cathode chamber and the gas mixes with and disperses into the catholyte and cathode (in the forms of dissolved gas and gas bubbles) thereby creating turbulence in the cathode chamber, and increase the space velocity of materials passing around the cathode. Feeding the composition of gas to the entire face of the cathode results in the gas permeating the entire electrode. This minimizes a downward partial pressure gradient of gas over the length of the reactor and provides a means for the mixing of materials throughout the cathode.

Flooding of the gas distributor pores with catholyte does not directly affect the activity of the cathode. This behavior is preferred in contrast to, e.g., a gas diffusion electrode which becomes essentially non-functional when flooded by liquid. The flooded gas distributor's pores can be cleared by means of elevated gas flow or pressure drop without concern for damaging the nearby electrode.

In some embodiments, the cathode is operated similarly to a trickle bed mode such that the cathode may be flooded with a higher volume of gas than liquid. As a result, the cathode retains a volume of gas held up within the porous electrode such that there is gas in contact with both the catholyte and the solid electrode phase. Furthermore, the entire cathode is flooded with the two-phase fluid composed of a gas and liquid, thereby permitting all of the cathode material to participate in the electrochemical process.

The gas and liquid phase materials may have several functions independently or in combination including, 1) providing turbulence, mixing and sheer flow to promote mass transport to and from the electrode surface; 2) delivering a reactant to be involved with an electrochemical transformation at the electrode; 3) flushing products or undesirable materials from the reactor; and 4) removing heat from the reactor.

Once the flooding and gas injection steps are carried out, and/or as they are being carried out, a voltage is applied to the cathode and electrode to initiate the electrochemical reaction, such as the reactions generally laid out in FIG. 1. The separator allows for selective passage of ions between electrodes while hydraulically and electrically separating electrode chambers, catholyte and anolyte fluids and materials contained therein. The separator is required to achieve selective and efficient transformation of electrochemically reactive materials under controlled process conditions, which can be significantly different between cathode and anode processes. Additionally, if anolyte and catholyte were permitted to mix, materials at the cathode might interfere or inhibit anodic processes, and vice versa. Also, if anolyte and catholyte are allowed to mix, materials consumed or produced at the cathode may be consumed or degraded at the anode, and vice versa. Process conditions and variables in the electrochemical reactor can vary, including but not limited to differences between the anode and the cathode such as changes in various aspects of the reaction conditions such as temperature, pressure, gas composition, catholyte composition, anolyte composition, solution pH, gas and liquid flow rates, current density and voltage.

In one aspect, the separator allows for the passage of ions between electrode chambers and electrodes which is required for charge balance in an electrochemical process. When electrons are transferred from the cathode to a reducible species in the catholyte this results in the buildup of excess negative charge on or near the cathode. To preserve charge balance in a continuous electrochemical process either an equal amount of positive charge must be transported to the cathode or the accumulated negative charge must be transported away from the cathode. Likewise, the analogous process occurs at the anode, or counter electrode, and this is the primary mechanism for continuous electrochemical charge and electron balance.

For the embodiments described herein, the transport of small, positively charged species, or cations, is more rapid and energy efficient for a cathodic process than transporting larger negatively charged species, or anions, away from the cathode. In some cases the cathodic (reduction) product cannot form without a supply of "excess" cations at the electrode process. An "excess" of cations is defined as when the number of positive charges exceeds the number of negative charges in solution at thermodynamic equilibrium. In the opposite sense, an "excess" of anions occurs when the number of negative charges exceeds the number of positive charges in solution at thermodynamic equilibrium.

The half reaction represented by Equation 1 is an example where a supply of "excess" cations is required at an electrode during the reduction process forming a charge-neutral product. The half reaction represented by Equation 2 is an example where the reduction products formed require a supply of "excess" cations for charge balance with charge-negative products.

$$CO_2 + 8H^+ + 8e^- \leftrightarrow CH_4 + 2H_2O \qquad \text{Equation 1:}$$

$$O_2 + H_2O + 2e^- \leftrightarrow HO_2^- + OH^- \qquad \text{Equation 2:}$$

To create a continuous supply of "excess" cations to support cathodic processes, an electrochemical oxidation of a material at the anode is used to cause an accumulation of excess positive charge at the anode in the form of small cations. Small cations include, for example, protons, deuterons, lithium ions, sodium ions, potassium ions, which have relatively high transport rates through liquid solutions and separators. The half reactions represented by Equation 3 and by Equation 4 are two examples of anodic (oxidation) reactions that can generate excess cations for transport to the cathode.

$$2H_2O \leftrightarrow 4e^- + O_2 + 4H^+ \qquad \text{Equation 3:}$$

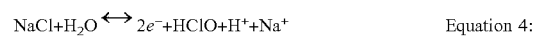

$$NaCl + H_2O \leftrightarrow 2e^- + HClO + H^+ + Na^+ \qquad \text{Equation 4:}$$

The overall result for a continuous electrochemical process is that for each electron consumed at the cathode, one electron is liberated at the anode and one positive charge, carried by a cation, transfers from anode to cathode; and for each electron liberated at the anode, one electron is consumed at the cathode and one negative charge, carried by an anion, transfers from cathode to anode. In an embodiment of the electrochemical reactor of the present disclosure the reaction at the cathode is enabled by the use of a separator that allows cationic species to selectively transport from anode to cathode. In another embodiment, the electrochemical reactor uses a separator that allows anionic species to selectively transport from anode to cathode.

Exemplary processes enabled by embodiments of the electrochemical reactor of the present disclosure include oxygen reduction to produce superoxide, hydrogen peroxide, hydroxide and other reduced oxygen-containing species, nitrate reduction to nitrogen gas, ammonia, hydroxide, water and other byproducts, as well as carbon dioxide reduction to hydrocarbon fuels and other chemicals. Additional embodiments disclose processes that incorporate elcetrocatalysts, as well as electron transfer agents and other reaction mediators which may be in a stationary phase or in a mobile fluid phase.

Hydrogen Peroxide Production

Oxygen ($O_2$) reduction at a cathode can be optimized to produce hydrogen peroxide ($H_2O_2$), peroxide ions ($HOO^-$), superoxide ($O_2$ radical anion) and hydroxide ions ($OH^-$) or water depending on the solution conditions. There are several steps that can occur during the electrochemical oxygen reduction mechanism. Two general reactions can be summarized as a two electron process or a four electron process in the following possible half reactions:

$$O_2+H_2O+2e^-=HO_2^-+OH^- \quad \text{Equation 5:}$$

$$O_2+2H_2O+4e^-=4OH^- \quad \text{Equation 6:}$$

Oxygen dissolved in water containing an electrolyte as a single liquid phase results in low productivity for either process on the industrial scale. In practice, gaseous oxygen is necessary to enhance the availability of oxygen at the electrode-electrolyte interface and to add turbulence and mixing for increased mass transport. Efficient and rapid production of hydrogen peroxide by the two electron process in Equation 5 is challenging due to relatively slow reduction kinetics and the required selectivity. Selectivity is dependent on the nature of the electrode surface, reduction overpotentials, electrode potential, partial pressure of oxygen, mass transport rates (flux) and solution conditions such as pH and temperature. The four electron process of Equation 6 is favored when mass transport is insufficient, the electrode potential too great and/or the electrode surface material is chosen to enhance the four electron process. If the electrode potential is too great and current density too high while under conditions favoring the two electron process in Equation 5 the peroxide species may also be reduced by an additional two electron process to hydroxide ions and/or water. Another competing and undesired reaction is the reduction (splitting) of water to hydrogen gas and hydroxide ions in Equation 7. This reaction is often a competing side-reaction during kinetically slow cathodic processes in general.

$$2H_2O+2e^-=H_2+2OH^- \quad \text{Equation 7:}$$

The following describes the catholyte, anolyte, and gas composition that can be used in hydrogen peroxide production processes according to methods described herein. In some embodiments, the co-generation of alkali and acids can be promoted during the production of hydrogen peroxide according to embodiments described herein. In some embodiments, the co-generation of chlorine, hypochlorous acid, and hypochlorite, or their bromine analogues, can be promoted during the production of hydrogen peroxide according to embodiments described herein.

The catholyte composition will generally include a liquid phase, and optionally an electrolyte and optionally an electrocatalyst. The catholyte liquid phase is water, or a mixture of water and a water soluble component such as an alcohol, glycol, or polyol. The catholyte liquid phase can contain a soluble, non-precipitating electrolyte or salt composed of cations including hydrogen, lithium, sodium and potassium, and anions including hydroxide, sulfate, bisulfate, chloride, bromide, iodide, nitrate, tetrahaloborates, hexahalophosphates, acetate, citrate, oxalate, salicylate, ethylene diacetate, propylene triacetate, and ethylenediamine tetraacetate. The catholyte can also have the composition of seawater. The catholyte liquid phase can optionally contain an electrocatalyst including quinones, hydroquinones, naphthoquinones and their derivatives, or transition metals complexed by polyaza macrocycles, porphyrin macrocycles, phthalocyanine macrocycles, and other chelating organic complexes.

The anolyte composition will generally include a liquid phase and an electrolyte where the anolyte liquid phase is typically water containing a soluble, non-precipitating electrolyte or salt composed of cations including hydrogen, lithium, sodium and potassium, and anions including hydroxide, sulfate, bisulfate, nitrate, phosphate, acetate, citrate, ethylene diacetate, propylene triacetate, and ethylenediamine tetraacetate. When co-generation of chlorine, hypochlorous acid, hypochlorite, bromine, hypobromous acid, or hypobromite are desired, chloride or bromide salts, such as hydrogen, lithium, sodium, potassium and calcium chloride or bromide, are included with the anolyte composition, while organic acid anions are excluded from the anolyte composition.

The gas composition will generally include an oxygen containing gas, such as air, oxygen enriched air, or pure oxygen.

Nitrate Destruction

Nitrate ($NO_3^-$) reduction at a cathode follows a complex series of reactions and transformations involving the transfer of one to eight electrons to nitrate yielding various products depending on solution pH, nitrate concentration, electrode surface and process conditions. The most desirable outcome for nitrate destruction is the five electron process yielding nitrogen gas in Equation 8.

$$NO_3^-+6H^++5e^-=\tfrac{1}{2}N_2+3H_2O \quad \text{Equation 8:}$$

$$NO_3^-+9H^++8e^-=NH_3+3H_2O \quad \text{Equation 9:}$$

Nitrate can be reduced exclusively to nitrogen gas on nickel or platinized nickel electrodes under alkaline conditions with high current efficiency provided that the electrode potential (or current density) is at an intermediate level and that a sweep of nitrogen and oxygen gas is present. A controlled amount of oxygen at the cathode during reduction enhances the rate of nitrate reduction. Under acidic conditions that are not proton limited, it is possible to reduce nitrate efficiently but the eight electron process in Equation 9 is favored to produce ammonia as the primary product. The ammonia generated could be used as a feedstock for producing chloramines for a water disinfection process, captured and transformed to ammonium hydroxide, or may be anodically oxidized to nitrogen gas. Nitrate reduction electrode potentials fall very close to that of water reduction and hydrogen evolution, particularly in acid solutions. Thus, water reduction and hydrogen evolution in acid solutions can be competing reactions with nitrate reduction and lead to decreases in current efficiency even though electrode-adsorbed hydrogen is thought to play an important role in certain nitrate reduction mechanisms.

The following describes the catholyte, anolyte, and gas composition that can be used in nitrate destruction processes according to methods described herein. Ammonia and nitrogen are formed by the reduction of nitrate.

The catholyte liquid phase may be water containing a composition of a nitrate salt and/or multiple nitrate salts and can include a soluble, non-precipitating electrolyte or salt composed of cations including hydrogen, lithium, sodium and potassium, and anions including hydroxide, sulfate, bisulfate, chloride, bromide, iodide, acetate, and citrate. The catholyte can also have the composition of regeneration fluid from a nitrate ion exchange resin.

The anolyte composition will generally include a liquid phase and an electrolyte where the anolyte liquid phase is typically water containing a soluble, non-precipitating electrolyte or salt composed of cations including hydrogen, lithium, sodium and potassium, and anions including hydroxide, sulfate, bisulfate, nitrate, phosphate, formate, acetate, citrate, ethylene diacetate, propylene triacetate, and ethylenediamine tetraacetate.

The gas composition will generally include a mixture of oxygen gas and non-reactive gas such as nitrogen, helium, neon, argon, krypton, xenon and carbon dioxide. The gas composition can be air, nitrogen enriched air, oxygen enriched air, or a pure non-reactive gas.

Carbon Dioxide Reduction

Carbon dioxide ($CO_2$) reduction at a cathode-supported electrocatalyst is a versatile method for forming a number of products useful for combustion fuels, chemical feedstocks, and precursors of each. The reduction products depend strongly on the electrocatalyst composition, the electrolyte fluid composition, pH, temperature and other operating parameters. Several common examples of $CO_2$ reduction products include carbon monoxide, ethylene, ethane, methanol, formic acid, and oxalic acid. Single carbon products such as carbon monoxide and methane follow two and eight electron processes in Equations 10 and 11, respectively.

$$CO_2 + 2H^+ + 2e^- = CO + H_2O \qquad \text{Equation 10:}$$

$$CO_2 + 8H^+ + 8e^- = CH_4 + 2H_2O \qquad \text{Equation 11:}$$

Higher carbon products (e.g., $C_2$ through $C_4$) follow more complex reaction pathways through a variety of intermediate steps. High selectivity and current efficiency can be obtained for several reactions leading to carbon monoxide, ethylene, methane, and formate. Product selectivity has a primary dependence on electrocatalyst composition and electrolyte conditions. Hydrogen evolution is a competing reaction in aqueous electrolytes and decreases current efficiency. But hydrogen plays an important role in hydrocarbon formation mechanisms and can be useful as a combustion product or synthesis gas precursor.

Chlorine Production

The above described process can be used to carry out production of chlorine, hypochlorous acid, or hypochlorite without hydrogen gas emissions. In such processes, a liquid catholyte, liquid anolyte and gas are fed into the process to prevent the evolution of hydrogen while promoting the production of chlorine, hypochlorous acid, or hypochlorite.

The catholyte composition will generally include a liquid phase, and optionally an electrolyte. The catholyte liquid phase is water. The catholyte liquid phase can contain a soluble, non-precipitating electrolyte or salt composed of cations including hydrogen, lithium, sodium and potassium, and anions including hydroxide, sulfate, bisulfate, chloride, bromide, iodide, nitrate, tetrahaloborates, hexahalophosphates, acetate, citrate, oxalate, ethylene diacetate, propylene triacetate, and ethylenediamine tetraacetate. The catholyte can also have the composition of seawater.

The anolyte composition will generally include a liquid phase and an electrolyte where the anolyte liquid phase is typically water containing a soluble, non-precipitating electrolyte or salt composed of cations including hydrogen, lithium, sodium and potassium, and anions including chloride, hydroxide, sulfate, bisulfate, and nitrate. The anolyte can also have the composition of seawater. The anolyte can also have the composition of the catholyte or cathode outlet stream.

The gas composition will generally include an oxygen containing gas including air, oxygen enriched air and pure oxygen.

All of the electrochemical reduction processes described above rely on the efficient mixing and distribution of liquid and gas phases over a solid electrode or electrocatalyst to achieve the intended outcome. Each of these processes has inherent kinetic limitations complicated by mass transport limitations of laminar two-phase flow, which leads to low productivity for a given reactor size. Electrochemical reactors disclosed herein are energy efficient, cost efficient, space efficient and are useful in on-site, and mobile systems and applications.

Superoxide Production

The production of superoxide occurs at the cathode as the first step in the electrochemical oxygen reduction mechanism proposed by Xu et al (J. Electroanalytical Chem. 410, pp. 235-242 (1996)) in Equations 12-15. The one electron reduction of molecular oxygen to the superoxide radical anion, Equation 12, is followed by several chemical and electrochemical steps, Equations 13-15, which can form hydrogen peroxide, sodium hydroxide and molecular oxygen depending on the process conditions and electrode activity. When superoxide and other intermediate species are adsorbed to the surface of the electrode the processes in Equations 13-15 are promoted.

$$O_2 + e^- = O_2^- \qquad \text{Equation 12:}$$

$$O_2^- + H_2O = HO_2 \cdot + OH^- \qquad \text{Equation 13:}$$

$$HO_2 \cdot + O_2^- = HO_2^- + O_2 \qquad \text{Equation 14:}$$

$$HO_2 \cdot + e^- \rightarrow HO_2^- \qquad \text{Equation 15:}$$

When superoxide resides in solution rather than adsorbed to the electrode it may be stabilized in aqueous alkaline media with its lifetime dependent on pH, salinity, ion pairing, temperature and reactive substrates. Estimates of superoxide half life in seawater are between approximately 5 and 9 minutes, see Millero, Geochmica et Cosmochimica Acta. Vol. 51, pp. 351-353 (1987). The lifetime of superoxide (100 micromolar initial concentration) produced by photolysis in aqueous alcohol solutions has been reported as 1.5 minutes at pH 11.0 and 41 minutes at pH 12.5, see McDowell, Inorganic Chem, Vol. 22, No. 5, pp. 847-848 (1983). The electrochemical reduction of molecular oxygen in anhydrous ionic liquids according to Equation 12 produces stable superoxide ions (AlNashef et. al., Electrochemical and Solid-State Letters, 4 (11), D16-D18, (2001)). Superoxide can also be purchased as an anhydrous solid such as potassium superoxide, $KO_2$, from industrial chemical suppliers.

Superoxide reacts with hydrogen peroxide in aqueous solution via the Haber-Weiss reaction in Equation 16 to produce molecular oxygen, hydroxyl radicals and hydroxide ions.

$$O_2^{.-} + H_2O_2 = O_2 + .OH + OH^- \quad \text{Equation 16:}$$

In the presence of hydrogen peroxide the hydroxyl radicals produced can also react with hydrogen peroxide producing water, superoxide and hydrogen ions in Equation 17.

$$.OH + H_2O_2 = H_2O + O_2^{.-} + H^+ \quad \text{Equation 17:}$$

Reactions in Equations 16 and 17 both consume hydrogen peroxide, but occurring together they have no net effect on superoxide concentration or pH.

Superoxide is thought to be an important reactive oxygen species for in-situ chemical oxidation (ISCO) and chemical oxidation of a variety of materials. In fact, superoxide radical anion is a mild reducing agent with a standard potential of −0.33 V, which makes it very effective for reacting with halocarbons. For example, superoxide is effective at breaking down non-aqueous phase liquids (NAPL) such as chloroform, perchloroethylene, tetrachloroethylene, polychlorinated biphenyls, fluorocarbons and perfluorooctanoic acid. Halocarbons are generally not affected by hydroxyl radicals. Superoxide, however, is not reactive to certain hydrocarbons such as benzene, toluene and alkanes. The combined presence of superoxide and hydroxyl radicals is known to be very effective for ISCO where a variety of contaminants are being oxidized. The combination of superoxide and hydroxyl radicals can be generated by activation of hydrogen peroxide solutions via the equilibrium reaction in Equation 17 (see Petri et. al., Fundamentals of ISCO Using Hydrogen Peroxide, Chapter 2, pp. 33-88 of "In Situ Chemical Oxidation for Groundwater Remediation", by R. L. Siegrist et. al. (2011)) or by the addition of potassium superoxide via the equilibrium reaction in Equation 16.

The short term stability of superoxide in aqueous alkaline solution is on the order of minutes and can enable the use of generated superoxide in the destruction of contaminants or other chemical transformations. In one embodiment, electrochemical reactors disclose herein are expected to be able to enhance the production of superoxide at the cathode in alkaline conditions to produce a cathode output solution containing a combination of hydrogen peroxide and superoxide, which in turn generates hydroxyl radicals by the Haber-Weiss reaction in Equation 16. Under suitable reactor conditions including current density, pH, and electrode activity, the production of superoxide as the sodium salt, $NaO_2$, can be significantly enhanced while reducing the production of hydrogen peroxide and alkali.

Alkaline Conditioning of Catholyte Feed

The presence of scaling ions or minerals which precipitate at alkaline pH (collectively referred to as sealants) can coat and passivate the cathode when the pH of the cathode feed solution, or catholyte, increases in the cathode flow chamber during the production of alkaline hydrogen peroxide or alkali. As a result of cathode passivation, the electrode activity is reduced and the efficiency of hydrogen peroxide and alkali production decreases. To avoid cathode passivation by precipitated materials at alkaline pH the cathode feed solution must be absent of sealants in concentrations greater than their solubility limits in an alkaline cathode product.

For example, at alkaline pH, magnesium sulfate (260 g/L cold water solubility) transforms to magnesium hydroxide (0.009 g/L cold water solubility) and precipitates from water above its solubility limit. Calcium chloride (745 g/L cold water solubility) transforms to calcium hydroxide (1.8 g/L cold water solubility) at alkaline pH. Magnesium and calcium materials are common constituents in salts such as sodium sulfate and sodium chloride commonly employed as catholyte electrolytes. Magnesium and calcium are also common constituents in water sources including tap water, ground water, seawater, and recycled water.

Removal of sealants from water and electrolytes fed to the cathode enables stable, continuous operation of the process and enables the use of a variety of water sources and purity grades of electrolytes. Sealant removal from a waste brine stream, such as a reverse osmosis reject stream from a desalination process, can enable the use of waste brine as a cathode feed solution. Likewise a similarly treated waste brine stream may also be suitable to use as an anode feed solution. In an embodiment, waste brine may be used in the electrochemical reactor of the present disclosure and would primarily contain the appropriate ions to produce chemicals such as hydroperoxides, alkali, acids, chlorine and other oxygen-based or halogen-based oxidants.

Scaling ions may be removed from the electrolyte feedstocks by conventional separation processes including nanofiltration, reverse osmosis, ion exchange, electrodeionization, thermal distillation and membrane distillation. These methods are useful for conditioning feed water containing high concentrations of scaling ions and other impurities not compatible with the reactor process.

Alternatively, scaling ions in low concentration may be precipitated by adjusting the pH of the cathode feed solution to alkaline pH greater than 9.5 or high enough to cause the scaling ions to precipitate out of the solution phase. This alkaline conditioning of the cathode feed solution is a lower cost alternative to conventional separation processes in cases where the precipitated suspended solids concentration and particle size are low enough to pass through the cathode chamber without affecting reactor performance, without coating the electrode, without accumulating in the reactor and without accumulating in the fluid handling system. In cases where the precipitated suspended solids concentration and particle size are large enough to settle, a settling tank or filter may be used to remove the precipitated solids upstream of the reactor.

Adjustment of the pH of the cathode feed solution is made upstream of the reactor and may be achieved by variety of methods including the dosing of a small side stream of the alkaline cathode product from the reactor into the cathode feed solution; dosing a bulk chemical such as sodium hydroxide or other alkaline material into the cathode feed solution; using alkaline process water from other site operations; or waste products such as alkaline desalination brine.

Maintaining Hydrogen Peroxide Production Efficiency During Cogeneration of Acids The cogeneration of acid with alkaline hydrogen peroxide in the electrochemical reactor creates a competing ion transport effect through the separator, which can impact hydrogen peroxide production efficiency, acid production efficiency and cathode performance. As the acid proton concentration increases in a salt brine anolyte during water oxidation at the anode the flux of acid protons through the separator increases relative to the flux of alkali metal cations including lithium ($Li^+$), sodium ($Na^+$) and potassium ($K^+$). For cation exchange separators such as Nafion 424, the molar flux of hydrogen cations is roughly equivalent to the molar flux of sodium cations at a $H^+:Na^+$ molar ratio of approximately 1:10, as estimated experimentally. Once the molar flux of hydrogen cations significantly exceeds the molar flux of alkali metal cations the excess of alkali metal cations required at the cathode for charge balance in the alkaline hydrogen peroxide production mechanism cannot be satisfied and the Faradaic efficiency for hydrogen peroxide production declines. Likewise, the increasing flux of hydrogen cations from the anode through the separator to cathode decreases the conversion efficiency of the anolyte alkali metal salt or electrolyte to the acid form.

The addition of alkali to the catholyte feed at a concentration slightly below and approaching that of the average catholyte output alkali concentration based on output pH, can maintain a suitable excess of alkali metal cations at the cathode to maintain a maximum Faradaic hydrogen peroxide production efficiency up to the approximate point where the molar flux of hydrogen cations overtakes the molar flux of alkali metal cations. Elevating the catholyte feed pH to nearly equivalent to or above the catholyte output pH results in a decrease in Faradaic hydrogen peroxide production efficiency overall until the flux of hydrogen cations from the anolyte balances with a portion of the added alkali in the catholyte.

Cathode Reactivation Process for Hydrogen Peroxide Production

Cathode performance for hydrogen peroxide production can degrade a number of ways including (1) idle periods greater than 48 hours, (2) exposure to acids, (3) excessive current density, (4) reverse polarization, (5) scaling or surface passivation, (6) metal deposition and additionally other chemical or physical processes which may alter the cathode surface. For performance degradation caused by (1) through (4), the cathode can be reactivated directly by a reactivation process. For degradation caused by (5), the scalant(s) may be flushed off with water and the cathode returned to service or the scalant(s) removed with acid flushing followed by a cathode reactivation process. For degradation caused by (6), the metal may be stripped off by acid flushing and/or by reverse polarization (e.g. anodic stripping) followed by a cathode reactivation process.

The cathode reactivation process can include chemical and electrochemical processes and may be conducted in-situ on a cathode installed in a reactor or ex-situ by removing the cathode from the reactor for treatment. In an embodiment, the cathode reactivation process is conducted in-situ. In preferred embodiments the cathode reactivation process incorporates electrochemical and chemical steps. In a preferred embodiment the cathode reactivation process incorporates an electrochemical reduction step, a chemical treatment step and an electrochemical conditioning step prior to returning the cathode to normal service. The cathode reactivation process will return the hydrogen peroxide production efficiency to its original level or greater in many cases.

Process Response to Feed Gas Composition

Most common gases have limited solubility in water. For example, at 1 atmosphere pressure and 25 degrees centigrade 100% oxygen gas has a solubility limit near 40 mg/L in pure water. As the concentration of oxygen decreases to the composition of air, 21% oxygen, the partial pressure of oxygen decreases resulting in a dissolved oxygen concentration near 8 mg/L in water. In the presence of electrolytes the solubility of oxygen decreases slightly.

The relatively low solubility of oxygen in water results in oxygen usually being the limiting reagent in the liquid catholyte for electrochemical oxygen reduction processes and often leads to low rates and efficiencies of oxygen reduction. The dissolution and diffusion rate of oxygen gas into and through the liquid catholyte to the electrode becomes a mass transport limitation as a result of the limited solubility of oxygen in the liquid catholyte. Common methods to increase the mass transport rate of oxygen gas to an electrode include the use of high pressure to increase dissolved oxygen concentration, enhanced gas bubble dispersion and mixing into the catholyte to increase dissolution rates, and simultaneous contact of gas bubbles and liquid electrolyte with the electrode surface at a common interface otherwise known as a triple phase boundary.

The electrochemical reactor, flow pathway and process design of the present disclosure can use all of the above methods to enhance mass transport rate. The present disclosure improves upon the methods of gas bubble dispersion, mixing and creating triple phase boundary area to overcome mass transport limitations posed by the solubility limit of a gas in an electrolyte solution to the point where elevated pressure does not further improve mass transport of gaseous materials to an electrode. The disclosed electrochemical reactor, flow pathway and process design can enable the use of lower pressures which results in significantly lower capital costs, operating costs and lower weight equipment compared to higher pressure rated equipment.

In an embodiment of the present disclosure, a gas is fed to the majority of the cathode surface by means of the gas distributor while the liquid catholyte, also known as the catholyte flow, is fed into a cathode flow channel entrance at one end of the flow channel. The liquid catholyte is introduced to the cathode parallel to the flow channel axis. Gas is introduced to the cathode perpendicularly with regard to the cathode flow channel axis. As the liquid catholyte flows through the cathode flow channel, parallel to the cathode, gas is being introduced into the liquid catholyte, creating a multiphase catholyte solution, and gas is also being introduced into the cathode via the gas distributor. Thus, the cathode surface is in intimate contact with both the gas and liquid components of the multiphase catholyte solution, also known as the cathode process fluid. The combination of the liquid and gas feeds then exit concurrently from the cathode flow channel exit.

In an embodiment, the gas volume is greater than 100 times the liquid volume at the cathode. In another embodiment, the total gas to liquid volume ratio at the cathode is between 300 and 600. In yet another embodiment, the total gas to liquid volume ratio at the cathode is between 600 and 1200. In some embodiments, total gas to liquid volume ratios at the cathode above about 1400 may be employed, but have not been found to provide significant improvement to the production of hydrogen peroxide.

In an embodiment of the electrochemical reactor of the present disclosure, the liquid anolyte, also known as the anolyte flow, can flow through an anolyte flow channel parallel to the anode and gas can be introduced into the liquid anolyte thus creating a multiphase anolyte solution while gas is also being introduced into the anode via the gas distributor.

Electrolytic processes are thought to benefit from excess gas volume to liquid volume at the cathode due to improved mass transport rates, gas dispersion uniformity, and fluid turbulence. For example, if the flow of liquid through the reactor is "surgy", indicating that a high degree of mixing is occurring between liquid and gas phases around the cathode surface, higher mass transfer rates of gaseous materials to and from the cathode surface will result. Additionally, the amount of liquid contacting the cathode surface is significantly reduced at gas to liquid volume ratios above 100 compared to gas to liquid volume ratios of 10 or less and approaching single-phase liquid flow thereby reducing the diffusion path length through a liquid phase coating the cathode, which will result in higher mass transfer rates of gaseous materials to the cathode surface.

High gas to liquid volumes at an electrode are typically expected to increase the resistivity of the process fluid resulting in increased cell voltages and power consumption. However, in embodiments of the electrochemical reactor of the present disclosure, this relationship has not been observed below a gas to liquid volume ratio of about 1400. Instead, the cell voltage is more sensitive to electrolyte strength at the anode when a cation exchange membrane is employed. The cell voltage is also sensitive to the overpotential or voltage polarization of the cathode, which has been observed to be dominated by the rates of reduction processes and the types of reduction processes occurring at the cathode.

Power Supply Configuration and Operating Sequence

The electrochemical reactor's power supply configuration is important for several aspects of operation, sitting idle, and cathode regeneration.

Figure 6:
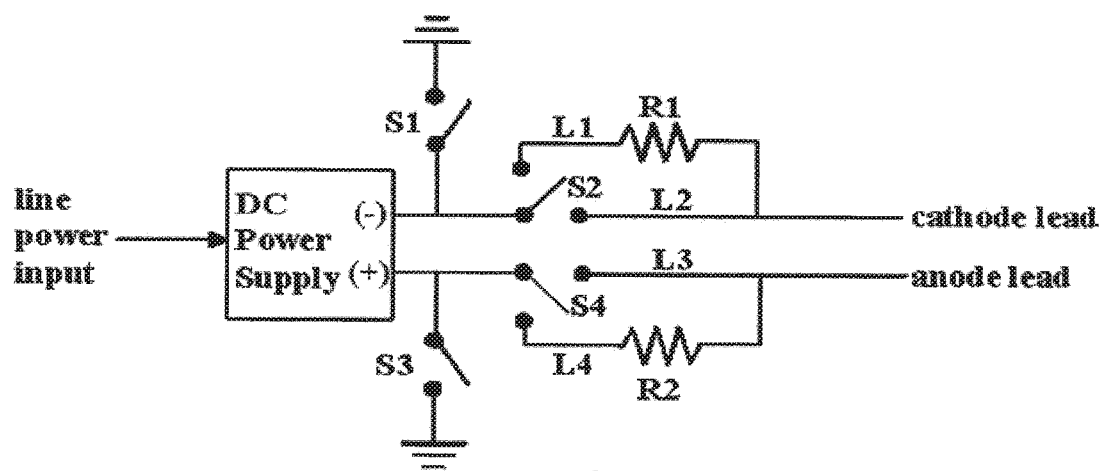
FIG. 6 depicts a schematic representation of a power supply for use with an electrochemical reactor.

An embodiment of a power supply providing direct current or modulated direct current to electrochemical reactors disclosed herein is depicted in FIG. 6. The power supply of FIG. 6 depicts a configuration that uses a direct current (DC) power supply with (−) and (+) output poles. The (−) and (+) poles may be connected to an external reference such as ground by means of closing switch 1 (S1) and switch 3 (S3), respectively. The (−) pole of the power supply is connected to the cathode of an electrochemical reactor by means of leg 1 (L1) or leg 2 (L2), either of which may be connected by means of switch 2 (S2). Similarly, the (+) pole of the power supply is connected to the anode of the electrochemical reactor by means of leg 3 (L3) or leg 4 (L4), either of which may be connected by means of switch 4 (S4).

Resistors R1 and R2 are used when there is an operating condition or process that requires their use. For example, when S1 is connected to ground and S2 is connected to L1 then R1 can be used to increase the voltage of the cathode lead relative to ground. Another example is when S4 is connected to L4 then R2 can be used to increase the load on the power supply preventing a capacitive "overload" condition on the power supply, which can be encountered for high surface area electrodes when direct current increases.

The DC power supply can be a linear DC power supply, a switching DC power supply, a modulated DC power supply with waveform generator, a DC-DC transformer or an alternating current (AC) rectifier with DC, modulated DC or pulsed DC outputs. The (−) pole of the power supply may be grounded while the (+) pole is polarized in voltage. Also, the (+) pole of the power supply may be grounded while the (−) pole is polarized in voltage. Also, when neither pole of the power supply is grounded the voltage "floats" or polarizes according to the load characteristics.

Switches S1 through S4 can be actuated mechanical contactors, magnetic solenoid contactors, magnetic relay switches or any other contactor which can completely electrically isolate the disconnected segment of a circuit.

Resistors R1 and R2 can be power resistors, resistive wire coil, or any other resistive element compatible with direct current having sufficient power rating and heat dissipation.

EXAMPLES

Example 1: Cathode Fouling with Precipitate and Cleaning

A reactor system containing an electrochemical reactor of FIG. 2A and fluid process flow illustrated in FIG. 4 were used in this example. The cathode's active superficial area was approximately 255 cm². The anolyte reservoir and chamber were charged with a 2.5 L solution of 0.75 molar sodium hydroxide in distilled water. The anolyte was recirculated through the anode chamber over time. A ca. 93% oxygen gas stream generated by a pressure swing adsorption oxygen concentrator was circulated through the gas feed line at a rate of 10-14 liters per minute at 2.9-3.3 psig. The catholyte was a 0.05 molar solution of sodium sulfate in distilled water fed into the catholyte feed line at a rate of 12.8 mL per minute at 1.3-1.6 psig (single pass, flow through). A DC current was applied to the reactor at 5.0 amps (current control) and approximately 1.9 volts measured between anode and cathode posts. The negative pole of the power supply was grounded. The catholyte output reached a steady state composition of 2800 to 2900 mg/L hydrogen peroxide at a pH of 12.4 during the first 2.5 hours of operation. By 3 hours of operation the catholyte output had decreased to 2600 to 2700 mg/L hydrogen peroxide at a pH of 12.4. The reactor was shut down after a total of 4 hours operation.

The reactor was restarted under the same conditions as above and the steady state catholyte output was 2400 mg/L hydrogen peroxide at pH 12.5 over 50 minutes of operation. A subsequent attempt to flush the cathode with catholyte solution did not make a significant improvement on cathode performance. The cathode was removed from the reactor for inspection and had varying amounts of white granular solid collected on its surface. The solid was flushed off of the cathode with distilled water having a pH of about 5.8. The cathode was reinstalled in the reactor and tested under the same conditions as above, but used 0.05 molar sodium chloride as the catholyte feed solution. The catholyte output recovered to a steady state of 2900-3000 mg/L hydrogen peroxide at pH 12.4 during four hours of operation. The sodium sulfate solution produced a faintly hazy suspension of precipitate when its pH was raised to 11.2, however the sodium chloride did not.)

Example 2: Alkaline pH Adjustment of Catholyte Feed

A reactor system with an electrochemical reactor of FIG. 2A and fluid process flow illustrated in FIG. 4 was used in this example. The cathode's active superficial area was approximately 255 cm². The anolyte reservoir and chamber were charged with a 2.5 L solution of 0.75 molar sodium hydroxide in distilled water. The anolyte was recirculated through the anode chamber over time. A ca. 93% oxygen gas stream generated by a pressure swing adsorption oxygen concentrator was circulated through the gas feed line at a rate of 11-14 liters per minute at 2.2-3.0 psig. The catholyte was a 0.05 molar solution of sodium sulfate in distilled water adjusted to pH 11.2 with sodium hydroxide to precipitate, presumably, trace magnesium. The alkaline catholyte solution with fine precipitate was fed into the catholyte feed line at a rate of 12.8 mL per minute at 0.9-1.4 psig (single pass, flow through). A DC current was applied to the reactor at 5.0 amps (current control) and approximately 2.0 volts measured between anode and cathode posts. The negative pole of the power supply was grounded. The catholyte output reached a steady state composition of 2900 to 3200 mg/L hydrogen peroxide at a pH around 12.25 during the 4.75 hours of operation. No loss of cathode performance was observed.

Example 3: Maintaining Hydrogen Peroxide Production Efficiency During Cogeneration of Acids at pH 11.2, Catholyte Feed A reactor system containing an electrochemical reactor of FIG. 2A and fluid process flow illustrated in FIG. 4 were used in this example. The cathode's active superficial area was approximately 255 cm². The anolyte reservoir and chamber were charged with a 2.5 L solution of 1.0 molar sodium sulfate in distilled water (pH 9.95). The anolyte was recirculated through the anode chamber over time. A ca. 93% oxygen gas stream generated by a pressure swing adsorption oxygen concentrator was circulated through the gas feed line at a rate of 12 liters per minute at 2.9 psig. The catholyte was a 0.05 molar solution of sodium sulfate in distilled water adjusted to pH 11.2 with sodium hydroxide to precipitate, presumably, trace magnesium. The alkaline catholyte solution with fine precipitate was fed into the catholyte feed line at a rate of 12.8 mL per minute at 1.3 psig (single pass, flow through). A DC current was applied to the reactor at 8.0 amps (current control) and approximately 3.30-3.37 volts measured between anode and cathode posts initially. The negative pole of the power supply was grounded. The catholyte and anolyte outputs over time are reported in Table 1.

The general trend was that as the anolyte pH decreased below 1.84 the hydrogen peroxide production efficiency decreased and the catholyte output pH decreased. The production run was terminated when the hydrogen peroxide production efficiency decreased below 40% Faradaic efficiency.

TABLE 1

| Elapsed Time (hours) | Hydrogen Peroxide Output Concentration (mg/L) | Hydogen Peroxide Faradaic Efficiency (%) | Catholyte Product pH | Anolyte Product pH |
| --- | --- | --- | --- | --- |
| 0.25 | 4700 | 71.1 | 12.68 | 2.59 |
| 1 | 4700 | 71.1 | 12.60 | 2.01 |
| 1.5 | 4650 | 70.4 | 12.59 | 1.84 |
| 2 | 4400 | 66.6 | 12.58 | 1.72 |
| 2.5 | 4300 | 65.1 | 12.53 | 1.62 |
| 3 | 4400 | 66.6 | 12.50 | 1.59 |
| 3.5 | 4300 | 65.1 | 12.45 | 1.52 |
| 4 | 4100 | 62.1 | 12.40 | 1.51 |
| 5.5 | 3600 | 54.5 | 12.23 | 1.39 |
| 6.5 | 3050 | 46.2 | 12.13 | 1.35 |
| 7.5 | 2600 | 39.4 | 11.96 | 1.32 |

Example 4: Maintaining Hydrogen Peroxide Production Efficiency During Co-Generation of Acids at pH 12.4, Catholyte Feed A reactor system containing an electrochemical reactor of FIG. 2A and fluid process flow illustrated in FIG. 4 were used in this example. The cathode's active superficial area was approximately 255 cm². The same cathode assembly was used as in Example 3. The anolyte reservoir and chamber were charged with a 2.5 L solution of 1.0 molar sodium sulfate in distilled water (pH 10.2). The anolyte was recirculated through the anode chamber over time. A ca. 93% oxygen gas stream generated by a pressure swing adsorption oxygen concentrator was circulated through the gas feed line at a rate of 12 liters per minute at 2.9 psig. The catholyte was a 0.05 molar solution of sodium sulfate in distilled water adjusted to pH 12.5 with sodium hydroxide to increase the "excess" sodium at the cathode and to precipitate, presumably, trace magnesium. The alkaline catholyte solution with fine precipitate was fed into the catholyte feed line at a rate of 12.8 mL per minute at 1.2 psig (single pass, flow through). A DC current was applied to the reactor at 8.0 amps (current control) and approximately 3.20-3.30 volts measured between anode and cathode posts initially. The negative pole of the power supply was grounded. The catholyte and anolyte outputs over time are reported in Table 2.

The general trend was that as the anolyte pH decreased below 1.70 the hydrogen peroxide production efficiency increased to its maximum until the anolyte pH decreased below 1.53 and the hydrogen peroxide production efficiency and catholyte output pH decreased. The production run was terminated when the hydrogen peroxide production efficiency decreased below 65% Faradaic efficiency.

TABLE 2

| Elapsed Time (hours) | Hydrogen Peroxide Output Concentration (mg/L) | Hydogen Peroxide Faradaic Efficiency (%) | Catholyte Product pH | Anolyte Product pH |
| --- | --- | --- | --- | --- |
| 0.5 | 4600 | 69.6 | 12.74 | 2.27 |
| 1 | 4500 | 68.1 | 12.67 | 1.98 |
| 1.5 | 4600 | 69.6 | 12.62 | 1.80 |
| 2 | 4600 | 69.6 | 12.62 | 1.70 |
| 2.5 | 4800 | 72.6 | 12.61 | 1.63 |
| 3 | 4900 | 74.2 | 12.57 | 1.56 |
| 3.5 | 4800 | 72.6 | 12.54 | 1.53 |
| 4 | 4500 | 68.1 | 12.49 | 1.50 |
| 4.5 | 4600 | 69.6 | 12.46 | 1.45 |
| 5 | 4500 | 68.1 | 12.42 | 1.42 |
| 5.5 | 4100 | 62.1 | 12.41 | 1.40 |

Example 5: Cathode Reactivation Process for Hydrogen Peroxide Production

This example discloses a baseline hydrogen peroxide production performance trial followed by an extended idle period and a second hydrogen peroxide performance trial to show reduced output. A subsequent cathode reactivation process is conducted and is followed by a third hydrogen peroxide performance trial to show recovered output performance. Hydrogen peroxide output and Faradaic efficiency for the three performance trials are displayed in FIG. 5.

The same reactor configuration and operating conditions were used for all performance trials in this example. A reactor system with the electrochemical reactor of FIG. 2A and fluid process flow illustrated in FIG. 4 was used in this example. The cathode's active superficial area was approximately 255 cm². The anolyte reservoir and chamber were charged with a 2.5 L solution of greater than 0.6 molar sodium hydroxide in distilled water. The anolyte was recirculated through the anode chamber over time. A ca. 93% oxygen gas stream generated by a pressure swing adsorption oxygen concentrator was circulated through the gas feed line at a rate of 12 liters per minute at 3.0 psig. The catholyte was a 0.05 molar solution of sodium sulfate in distilled water adjusted to pH 11.2-11.4 with sodium hydroxide to precipitate, presumably, trace magnesium. The alkaline catholyte solution with fine precipitate was fed into the catholyte feed line at a rate of 12.8 mL per minute at 1.3 psig (single pass, flow through). A DC current was applied to the reactor at 8.0 amps (current control) and approximately 2.3-2.4 volts measured between anode and cathode posts initially. The negative pole of the power supply was grounded.

Figure 5:
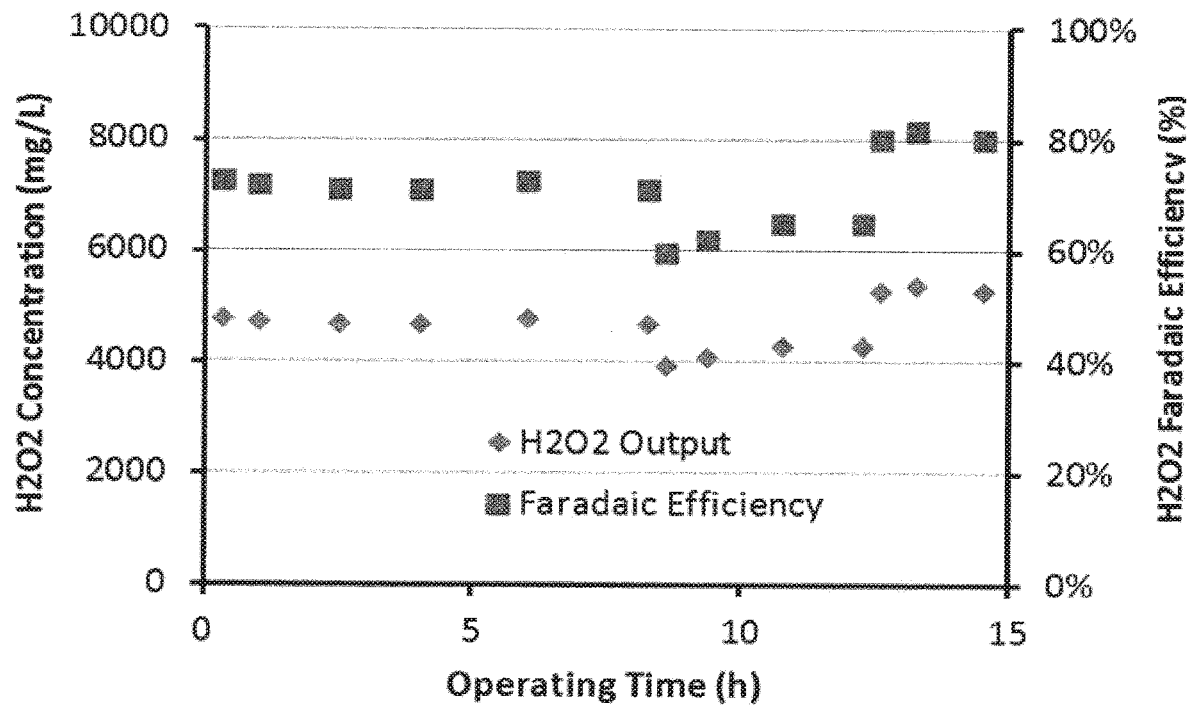
FIG. 5 is a graphical representation of hydrogen peroxide output and faradaic efficiency for three performance trials.

The reactor was operated in the above manner for three performance trials with hydrogen peroxide output and Faradaic efficiency displayed in FIG. 5. The first trial was from 0 to 8.25 hours having an average hydrogen peroxide output concentration near 4750 mg/L and average pH of 12.61, output solution temperature 21-22 degrees C. The average Faradaic efficiency for hydrogen peroxide production was 71.8%. The reactor was then left idle for 14.75 days without draining its fluids.

The second trial was conducted after 14.75 days of idle time, results displayed from 8.5 to 12.25 hours in FIG. 5. This trial had a lower average hydrogen peroxide output concentration near 4150 mg/L and average pH of 12.64, output solution temperature 20-21 degrees C. The average Faradaic efficiency for hydrogen peroxide production was 63.0% showing a reduced output performance due to degraded cathode activity for hydrogen peroxide production.

After the second trial with reduced output performance, a cathode reactivation process was conducted in-situ using the same reactor and process configuration described above, but with modified operating and feed parameters.

The cathode reactivation process followed three steps.

Step 1—electrochemical reduction of cathode: The anolyte was a 2.5 L solution of greater than 0.6 molar sodium hydroxide in distilled water. The anolyte was recirculated through the anode chamber. An air gas stream was pumped through the gas feed line at a rate of 5 liters per minute at 2.2 psig. The catholyte was a 0.05 molar solution of sodium sulfate in distilled water adjusted to pH 11.2-11.4 with sodium hydroxide. The catholyte solution was fed into the catholyte feed line at a rate of 12.8 mL per minute at 0.9 psig (single pass, flow through). A DC current was applied to the reactor at 10.0 amps (current control) with floating potentials (not grounded) and the cell potential increased from 3.40 V to 3.86 V over the 15 min reduction period.

Step 2—activation solution flush: The power supply was turned off and the air feed reduced to 1 liter per minute while an activation solution was fed into the catholyte feed line in place of the original catholyte. A 400 mL activation solution containing 0.1 molar sodium sulfate, 0.2 molar sodium hydroxide and approximately 2.4 millimolar peroxyacetic acid was flushed through the cathode chamber of the electrochemical reactor over 30 minutes. The peroxyacetic acid was made by mixing 3.2 mL of 1.0% hydrogen peroxide solution at pH 12.2 with 0.10 g of triacetin at room temperature and adding that solution to the activation solution.

Step 3—cathode conditioning: The original catholyte was fed into the catholyte feed line at 12.8 mL/min, as in Step 1, and the air feed increased to 6 liters per minute. The power supply was turned on and a DC current was applied to the reactor at 5.0 amps (current control) and the cell voltage stabilized at 2.94 volts. After 15 minutes, the system was completely shut down concluding the cathode reactivation process.

The third trial was conducted immediately after the cathode reactivation process and the results are displayed from 12.5 to 14.5 hours in FIG. 5. This trial used the same reactor, process configuration, operating and feed parameters as the first two trials above. This trial had a higher average hydrogen peroxide output concentration near 5300 mg/L and average pH of 12.62, output solution temperature 20-21 degrees C. The average Faradaic efficiency for hydrogen peroxide production was 80.7% showing an output performance which was slightly greater than the first trial's baseline performance.

Example 6: Superoxide Production

Evidence for enhanced superoxide production was observed using the electrochemical reactor of FIG. 2A and process flow of FIG. 4. At 5 amps a relatively low hydrogen peroxide production current efficiency is less than 60% is accompanied by a lower than normal pH (e.g., 2000-2400 mg/L hydrogen peroxide and pH 12.40). As the current density is increased to 8 amps the hydrogen peroxide production current efficiency decreases rapidly to less than 40% and the pH decreases by at least 0.1 pH units (e.g., 2600 mg/L hydrogen peroxide and pH 12.26). If the loss of hydrogen peroxide production efficiency was due to current going into the four electron reduction of molecular oxygen in Equation 2 or the splitting of water in Equation 3, then a significant amount of hydroxide would be generated thereby raising the pH significantly, which is not observed. Furthermore, significant electrolytic splitting of water at the cathode would require a larger overpotential at the cathode (ca. 0.5 V more negative) and be reflected in a higher cell voltage. However, the cell voltage remains unchanged relative to higher efficiencies as in the examples above.

Additional evidence in support of superoxide production is the decoloration of methylene blue dye with the fresh cathode output solution produced with the above characteristics. A 25 mg/L solution of methylene blue can be decolorized to the eye, partially within minutes and completely within 5 hours of mixing with the aforementioned freshly produced cathode product (e.g., 2600 mg/L hydrogen peroxide and pH 12.26). The decoloration of methylene blue does not occur on this time scale or at all when using catholyte product aged for at least 24 hours or using store bought hydrogen peroxide to make a simulated catholyte product in control experiments. The decoloration of methylene blue dye is thought to be caused by or at least initiated by the direct action of generated superoxide or by the evolution of hydroxyl radicals via the Haber-Weiss reaction in Equation 16 over time relative to the control experiments.

Example 7: Alkaline Hydrogen Peroxide Production

A reactor system with the reactor of FIG. 2A and fluid process flow illustrated in FIG. 4 was used in this example. The cathode's active superficial area was approximately 255 $cm^2$. The anolyte reservoir and chamber were charged with a 1.5 molar solution of sodium hydroxide in distilled water, reused from previous trials. A ca. 93% oxygen gas stream generated by a pressure swing adsorption oxygen concentrator was fed into the gas feed line at a rate of 6 liters per minute at 1.8 psig. Distilled water was fed into the catholyte feed line at a rate of 13 mL per minute at approximately 0.8 psig. A DC current was applied to the reactor at 5.0 amps and 2.35-2.40 volts. The catholyte output reached a steady state composition of 1400 to 1440 mg/L hydrogen peroxide at a pH of 12.6 within ten minutes of applying the electric current and remained there with an output product temperature of 17.5 to 18.1 degrees Centigrade until the process conditions were changed after 60 minutes.

Example 8: Cogeneration of Alkaline Hydrogen Peroxide and Citric Acid

A reactor system with the reactor of FIG. 2A and fluid process flow illustrated in FIG. 4 was used in this example. The cathode's active superficial area was approximately 255 $cm^2$. The anolyte reservoir and chamber were charged with a 10% weight to volume solution of trisodium citrate in distilled water. A filtered compressed air stream was fed into the gas feed line at a rate of 5 liters per minute at 1.3 psig. A solution of 0.05 molar sodium sulfate and 0.01 molar sodium chloride in distilled water was fed into the catholyte feed line at a rate of 13 mL per minute at approximately 1.0 psig. A DC current was applied to the reactor at 5.0 amps and 4.55-4.65 volts. The catholyte output reached a steady state composition of 720 mg/L hydrogen peroxide with a pH of 12.4 (pH measured at a 20-fold dilution) within twelve minutes of applying the electric current and remained there at ambient temperature near 15 degrees centigrade until the process conditions were changed after 29 minutes. The air feed rate was then increased to ca. 15 liters per minute at 2 psig. The catholyte inlet pressure increased to 1.5 psig. The DC current was maintained at 5.0 amps while the voltage increased to 4.74 volts. The catholyte output reached a new steady state composition of 1040 to 1080 mg/L hydrogen peroxide at a pH of 12.3 (pH measured at a 20-fold dilution) within five minutes of changing the air feed rate until the reactor was shut down after 46 minutes.

To the existing catholyte feed was added 0.001 molar trisodium citrate and the reactor restarted under the previous process conditions and nearly the same catholyte output was achieved at 1000-1080 mg/L hydrogen peroxide at a pH of 12.3 decreasing to 12.0 (pH measured at a 20-fold dilution) during the first 35 minutes of operation. While maintaining the current at 5.0 amps (air feed was reduced to 5 liters per minute at 46 minutes) the pH of the catholyte output continued to decrease to a pH of 10.2 (not diluted) at 2 hours 25 minutes when the system was shut down. The anolyte solution was drained from the reactor and had a pH of 2.5 indicating the production of citric acid.

Example 9: Generation of Hydrogen of Alkaline Hydrogen Peroxide and Sulfate Acids A reactor system with the reactor of FIG. 2A and fluid process flow illustrated in FIG. 4 was used in this example. The cathode's active superficial area was approximately 255 cm$^2$. The anolyte reservoir and chamber were charged with a 1.9 L solution of 0.25 molar sodium sulfate in distilled water, initial pH=9.5. A ca. 93% oxygen gas stream generated by a pressure swing adsorption oxygen concentrator was circulated through the gas feed line at a rate of 14.5 liters per minute at 2.9 psig. A 0.02 molar solution of sodium sulfate in distilled water was fed into the catholyte feed line at a rate of 12.8 mL per minute at 1.5 psig. A DC current was applied to the reactor at 7.0 amps and 3.7 volts between anode and cathode posts. The catholyte output reached a steady state composition of 2400 to 2450 mg/L hydrogen peroxide at a pH of 12.5 within twenty minutes of applying the electric current and remained there with an output product temperature of 19 to 20 degrees Centigrade until about 60 minutes. Over the following 75 minutes the hydrogen peroxide output concentration decreased to about 2000 mg/L with a pH of 12.5 and temperature increasing to 21 degrees Centigrade. The process was shut down after a total operating time of 135 minutes. The total collected hydrogen peroxide product stream had a volume of 1.7 L with a measured composition of 2300 mg/L hydrogen peroxide at pH 12.5. The anolyte was removed from the reactor with a volume of 1.8 L and a measured pH of 1.42 indicating conversion of sodium sulfate to its acid forms. The hydrogen peroxide and anolyte product streams were combined producing a pH neutralized product with a measured composition of 1050 mg/L hydrogen peroxide at a pH of 9.8, 0.2 pH units higher than the starting anolyte solution, and a calculated sodium sulfate content of 0.15 molar concentration.

Example 10: Cogeneration of Alkaline Hydrogen Peroxide and Sodium Hypochlorite A reactor system with the reactor of FIG. 2A and fluid process flow illustrated in FIG. 4 was used in this example. The cathode's active superficial area was approximately 255 cm$^2$. The anolyte reservoir and chamber were charged with a 1.8 L solution of 0.25 molar sodium hydroxide and 0.067 molar sodium chloride in distilled water, initial pH=13.2. A ca. 93% oxygen gas stream generated by a pressure swing adsorption oxygen concentrator was circulated through the gas feed line at a rate of 14.5 liters per minute at 3.0 psig. A 0.02 molar solution of sodium sulfate in distilled water was fed into the catholyte feed line at a rate of 12.8 mL per minute at 1.7 psig. A DC current was applied to the reactor at 7.0 amps and 2.7 volts between anode and cathode posts. The catholyte output reached a steady state composition of 2300 to 2450 mg/L hydrogen peroxide at a pH of 12.6 within twenty minutes of applying the electric current and remained there with an output product temperature of 19 to 21 degrees Centigrade until the process was shut down after 138 minutes of operation. The final output pH had decreased slightly to 12.5. The total collected hydrogen peroxide stream had a volume of 1.7 L with a measured composition of 2350 mg/L hydrogen peroxide at pH 12.6. The anolyte was removed from the reactor with a volume of 1.75 L and a measured pH of 12.0. The total chlorine content was measured to be near 40 mg/L+/−10 mg/L.

Example 11: Process Response to Feed Gas Composition

An example of the mass transport rate benefits in the present disclosure is reported in Table 3 for alkaline hydrogen peroxide production by electrolytic oxygen reduction. The results also illustrate the response of hydrogen peroxide output, pH and cell voltage response as oxygen reduction efficiency decreases. The total gas to liquid volume ratio at the cathode was kept constant near 1200 while the oxygen concentration was varied between about 93% (generated by a pressure swing absorption air separator) and about 21% from compressed air. The concentration of about 60% was produced by mixing equal volumes, at equal pressure, of 93% oxygen and air feed flow at the gas inlet. The reactor was operated in the same manner as described in Example 7, but with a total gas feed flow rate of 14 liters per minute at a feed pressure of 3.1 psig and a catholyte feed solution of 0.05 molar sodium sulfate. Readings were taken after 45 minutes of operation to allow the process to achieve steady-state output.

The results in Table 3 show that hydrogen peroxide and sodium hydroxide productivity and production ratios did not significantly change until the oxygen concentration was at 21%. At 21% oxygen feed, the hydrogen peroxide output decreased while pH and cell voltage increased most significantly; indicating that the process was less current efficient for oxygen reduction to hydrogen peroxide. The results at 21% oxygen feed also show that some current was going into undesirable reduction processes, which occur at more negative cathode voltages to produce hydroxide such as Equation 6 (four electron oxygen reduction process) and Equation 7 (water splitting). Results of the 93% and 60% oxygen feed trials demonstrate the high rate of mass transport of oxygen to the cathode surface in this reactor design, even at significantly reduced partial pressures of oxygen. Limitations of hydrogen peroxide production efficiency under the test conditions are likely occurring for reasons other than mass transport and may be related to electroactive electrode surface area and the balance of oxygen reduction pathways promoted by the electrode activity.

TABLE 3

| Oxygen Concentration in Feed Gas | Catholyte Output $H_2O_2$ Concentration | Catholyte Output pH | Cell Voltage |
|---|---|---|---|
| 93% | 2300 mg/L | 12.30 | 1.88 V |
| 60% | 2300 mg/L | 12.33 | 2.06 V |
| 21% | 1200 mg/L | 12.45 | 2.50 V |

Example 12: Power Supply Sequence for Hydrogen Peroxide Production

The use of a power supply schematically depicted in FIG. 6 with an electrochemical reactor depicted in FIG. 2A for the production of hydrogen peroxide, such as in Example 5 above, included the following sequences:
Startup:
 1. Turn on reactor gas and liquid feeds.
 2. Close S1 to connect ground, close S2 to connect L2 and close S4 to connect L4. S3 Remains open. R2 was 0.16 ohms.
 3. Turn on power supply output to a fixed current for normal operation.
Shut Down:
 1. Turn off power supply, allow primary electrical discharge to occur down to ca. 0.70 volts or less cell voltage.
 2. Open S1, S2 and S4. Power supply is in its idle state.
 3. Turn off reactor gas and liquid feeds. Reactor is in its idle state.

In the idle state, if the cathode remains grounded and connected to the power supply, the activated cathode surface for hydrogen peroxide production can be degraded more rapidly as residual charge in the power supply trickles to the electrodes over several hours.

Example 13: Power Supply Sequence for Cathode Reactivation Process for Hydrogen Peroxide Production The following sequence may be used for the cathode reactivation process described in Example 5 above:
Electrochemical Reduction of Cathode:
 1. Turn on reactor gas and liquid feeds.
 2. Close S3 to connect ground, close S2 to connect L2 and close S4 to connect L4. S1 Remains open. R2 was 0.16 ohms.
 3. Turn on power supply output to a fixed current for normal operation.
 4. After a specified time turn off power supply and allow primary electrical discharge to occur down to ca. 0.70 volts or less cell voltage.
 5. Open S3, S2 and S4. Power supply is in its idle state.
Activation Solution Flush:
 1. Power supply remains in its idle state.
Cathode Conditioning
 1. Close S1 to connect ground, close S2 to connect L1 and close S4 to connect L4. S3 Remains open. R1 was 0.035 ohms.
 2. Turn on power supply output to a fixed current for conditioning.
 3. After a specified time turn off power supply and allow primary electrical discharge to occur down to ca. 0.70 volts or less cell voltage.
 4. Open S1, S2 and S4. Power supply is in its idle state.
 5. Turn off reactor gas and liquid feeds. Reactor is in its idle state.

In view of the many possible embodiments to which the principles of the disclosure may be applied, it should be recognized that the embodiments herein should not be taken as limiting the scope of the present disclosure.

The invention claimed is:

1. A method for producing a chemical product including hydrogen peroxide, the method comprising:
 introducing a liquid anolyte into a first half-cell of an electrochemical reactor, wherein at least one chemical species of said liquid anolyte is oxidized at an anode electrode of the first half-cell;
 introducing a liquid catholyte into a cathode chamber of a second half-cell of the electrochemical reactor, wherein a porous cathode electrode permeable to gas and liquid is disposed in the cathode chamber;
 introducing a feed of a gas into the cathode chamber through an electrically-nonconductive, hydrophobic, gas-permeable gas distributor to mix with said liquid catholyte and create in the cathode chamber a multiphase catholyte solution including a liquid phase and a gas phase with the multiphase catholyte solution in contact with the cathode electrode;
 generating hydrogen peroxide in the cathode chamber, comprising reducing at least one chemical species of said multiphase catholyte solution at said cathode electrode;
 removing a reduced multiphase catholyte product comprising the hydrogen peroxide from said second half-cell and removing an oxidized liquid anolyte product from said first half-cell; and
 after performing the generating hydrogen peroxide for a period of time, discontinuing operation of the electrochemical reactor to stop the generating hydrogen peroxide, after the discontinuing performing a catholyte electrode reactivation process and after performing the catholyte electrode reactivation process re-commencing operation of the electrochemical reactor to re-restart the generating hydrogen peroxide, wherein the catholyte electrode reactivation process comprises:
  subjecting the cathode electrode in the cathode chamber to electrochemical reduction; and
  flushing the cathode electrode in the cathode chamber with an activation solution comprising peroxyacetic acid;
 and wherein:
 the electrochemical reactor further comprises:
  an ion permeable separator separating the first half-cell and the second half-cell, wherein the ion permeable separator is disposed to one side of the cathode electrode and the gas distributor is disposed to an opposing side of the cathode electrode;
  a housing enclosing the first half-cell, the second half-cell and the ion permeable separator; and
  a gas chamber disposed within the housing and located on a side of the gas distributor opposite the cathode chamber and the cathode electrode; and
 the generating hydrogen peroxide comprises applying electrical power to the electrochemical reactor to provide electrical current through an electrical current conduction path through the electrochemical reactor, the electrical current conduction path including the anode electrode and the cathode electrode and not including the gas distributor.

2. The method of claim 1, comprising during the generating hydrogen peroxide, also generating superoxide in the cathode chamber, and wherein the multiphase catholyte product comprises hydrogen peroxide and superoxide.

3. The method of claim 1, wherein the electrochemical reactor has a tubular configuration comprising the anode electrode, the ion permeable separator, the cathode electrode and the gas distributor as nested tubular features within a tubular containment boundary of the housing.

4. The method of claim 3, wherein the gas chamber comprises an annular space disposed between the tubular containment boundary and the gas distributor.

5. The method of claim 1, comprising prior to the introducing the gas into the cathode chamber through the gas distributor, flooding the cathode chamber, from the gas distributor through the cathode electrode to the ion separator, with the catholyte solution.

6. The method of claim 1, wherein during the generating hydrogen peroxide, the introducing the feed of the gas comprises introducing the feed of the gas into the cathode chamber through the gas distributor with a pressure differential across the gas distributor between the gas chamber and the cathode chamber in a range of from 0.5 to 15 psig.

7. The method of claim 1, wherein during the generating hydrogen peroxide, the introducing the feed of the gas comprises introducing the feed of the gas into the cathode chamber through the gas distributor with a differential pressure across the gas distributor between the gas chamber and the cathode chamber in a range of from 0.5 to 15 psig and at volume flow rate of the gas feed to the cathode chamber of from 100 to 1400 times greater than a liquid flow rate of the catholyte solution to the cathode chamber.

8. The method of claim 7, wherein volume flow rate of the gas feed is in a range of from 3 to 70 milliliters per minute per square centimeter of a surface area of the gas distributor exposed to the cathode chamber.

9. The method of claim 7, wherein the gas introduced into the cathode chamber through the gas distributor comprises at least 20% oxygen.

10. The method of claim 7, wherein the cathode electrode has a superficial area disposed toward the gas distributor, and the cathode electrode has a surface area of greater than 10 m$^2$ per m$^2$ of the superficial area of the cathode electrode.

11. The method of claim 10, wherein the cathode electrode comprises continuous carbon fibers.

12. The method of claim 1, wherein the cathode electrode has a thickness between the gas distributor and the ion permeable membrane in a range of from 0.1 to 10 millimeters.

13. The method of claim 12, wherein the gas distributor has a thickness between the gas chamber and the cathode chamber in a range of from 1 to 10 millimeters.

14. The method of claim 13, wherein the gas distributor has a pore diameter rating of less than 10 microns.

15. The method of claim 1, wherein
the gas distributor comprises a non-conductive, hydrophobic material selected from the group consisting of polyethylene, polypropylene, polytetrafluoroethylene and polyvinylidene difluoride.

16. The method of claim 1, comprising;
subjecting the multiphase catholyte product to gas-liquid separation to separate the multiphase catholyte product into a separated gas and a separated liquid; and
recycling at least a portion of the separated gas to prepare the feed of the gas to the gas distributor and not recycling any of the separated liquid to the cathode chamber.

17. The method of claim 1, wherein during the generating hydrogen peroxide, the entire cathode electrode is flooded with the multi-phase catholyte fluid.

18. The method of claim 1, wherein the reduced multiphase catholyte product has a pH of greater than pH 12.

19. A method for producing a chemical product including hydrogen peroxide, the method comprising:
introducing a liquid anolyte into a first half-cell of an electrochemical reactor, wherein at least one chemical species of said liquid anolyte is oxidized at an anode electrode of the first half-cell;
introducing a liquid catholyte into a cathode chamber of a second half-cell of the electrochemical reactor, wherein a porous cathode electrode permeable to gas and liquid is disposed in the cathode chamber;
introducing a feed of a gas into the cathode chamber through a gas-permeable gas distributor to mix with said liquid catholyte and create in the cathode chamber a multiphase catholyte solution including a liquid phase and a gas phase with the multiphase catholyte solution in contact with the cathode electrode, wherein the gas distributor is an electrically non-conductive, hydrophobic material;
generating hydrogen peroxide in the cathode chamber, comprising reducing at least one chemical species of said multiphase catholyte solution at said cathode electrode; and
removing a reduced multiphase catholyte product comprising the hydrogen peroxide from said second half-cell and removing an oxidized liquid anolyte product from said first half-cell;
wherein:
the electrochemical reactor comprises an ion permeable separator separating the first half-cell and the second half-cell;
the ion permeable separator is disposed to one side of the cathode electrode and the gas distributor is disposed to an opposing side of the cathode electrode;
the electrochemical reactor comprises a housing enclosing the first half-cell, the second half-cell and the ion permeable separator; and
the electrochemical reactor comprises a gas chamber disposed within the housing and located on a side of the gas distributor opposite the cathode chamber and the cathode electrode; and
the method further comprises after performing the generating hydrogen peroxide for a period of time, discontinuing operation of the electrochemical reactor to stop the generating hydrogen peroxide, after the discontinuing performing a catholyte electrode reactivation process and after performing the catholyte electrode reactivation process re-commencing operation of the electrochemical reactor to re-restart the generating hydrogen peroxide, wherein the catholyte electrode reactivation process comprises:
subjecting the cathode electrode in the cathode chamber to electrochemical reduction; and
flushing the cathode electrode in the cathode chamber with an activation solution comprising peroxyacetic acid.

20. The method of claim 19, wherein the cathode electrode has a superficial area disposed toward the gas distributor, and the cathode electrode has a surface area of greater than 10 m$^2$ per m$^2$ of the superficial area of the cathode electrode.

* * * * *